United States Patent [19]

Kinghorn et al.

[11] Patent Number: 5,198,427
[45] Date of Patent: Mar. 30, 1993

[54] NATURAL INTENSE SWEETENERS

[75] Inventors: A. Douglas Kinghorn, Chicago, Ill.; Young-Hee Choi, Seoul, Rep. of Korea

[73] Assignee: Research Corporation Technologies, Inc., Tucson, Ariz.

[21] Appl. No.: 549,776

[22] Filed: Jul. 9, 1990

[51] Int. Cl.$^5$ .................... A61K 35/00; A61K 31/705
[52] U.S. Cl. ........................... 514/26; 424/439; 426/534; 426/548; 426/658; 426/660; 514/175; 536/6; 540/115
[58] Field of Search ................ 424/439; 426/534, 548, 426/658, 660; 514/26, 175; 536/6; 540/115

[56] References Cited

PUBLICATIONS

*Pharm. J. Trans. Third Ser.* 24: 937–938 (May 1894) David Hooper "Abrus Precatorius; A Chem. Examination of the Leaves and Roots".
*Nigerian Journal of Pharmacy* vol. 12, No. 2 (Mar.–Apr. 1981) B. A. Akinloye, et al. "Abrus Precatorius Leave-A Source of Glycyrrhizin".
*J. Chem. Soc., Chem. Commun.*, pp. 1197–1198 (1982) Hson-Mou Chang, et al. "Isolation and Structure Elucidation of Abruslactone A: a New Oleanene-".
Kusama et al.; Agric. Biol. Chem. 50(10):2445–2451 (1986).
Nishizawa et al.; Tet. Lett. 29(36):4597–4598 (1988).
Markham et al.; Phytochemistry 28(1):299–301 (1988).
Takeshita et al.; Chem. Pharm. Bull. 37(3):846–848 (1989).
Choi et al.; J. Chem. Soc., Chem. Commun. 13:887–888 (Jul. 1, 1989).
Choi et al.; J. Nat. Prod. 52(5):1118–1127 (Sep./Oct. 1989).
Fullas et al.; Planta Med. 56(3):332–333 (Jun. 1990).
Sakai et al.; Chem. Pharm. Bull. 38(3):824–826 (Mar. 1990).
*The Merck Index;* 10th Ed. p. 647 (1985).
Goodman & Gilman's; *The Pharmacological Basis of Therapeutics;* 7th Ed. pp. 946–947; (1985).

*Primary Examiner*—Johnnie R. Brown
*Assistant Examiner*—Nancy S. Carson
*Attorney, Agent, or Firm*—Scully, Scott, Murphy & Presser

[57] ABSTRACT

The present invention relates to novel sweet compounds derived from the leaves of the subtropical weed *Abrus precatorius,* and their use as sweeteners. In particular, the present invention contemplates four novel sweet compounds isolated from *A. precatorius* or *A. fruticulosus,* and particularly, Abrusosides A, B, C and D and related compounds. The present invention also contemplates the use of these abrusosides and related compounds as sugar substitutes. The present invention contemplates the use of Abrusosides A–D as individual components or in mixtures, in a method for sweetening comestibles, foodstuffs, beverages and medicinal agents.

22 Claims, 4 Drawing Sheets

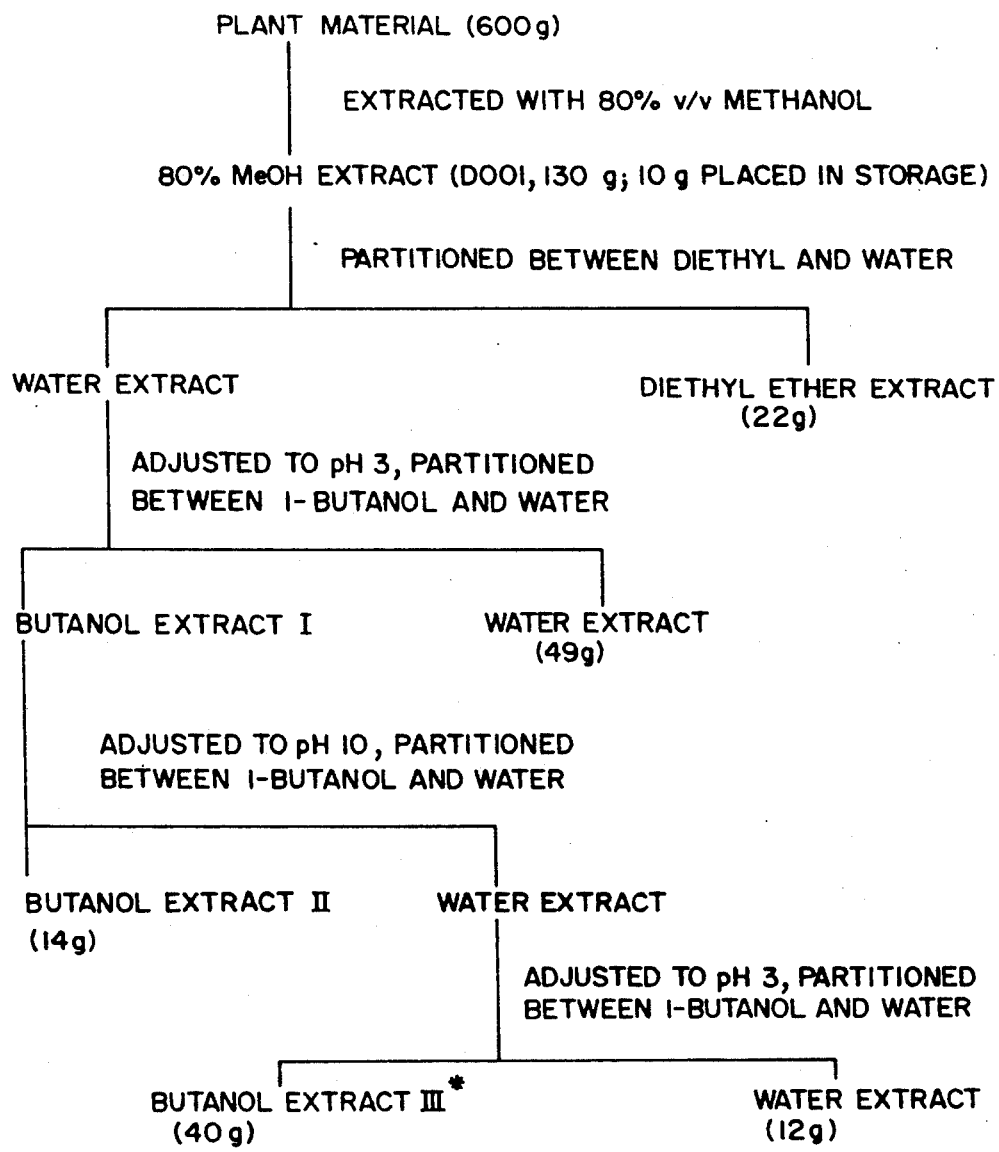
FIG.1 EXTRACTION AND PARTITION SCHEME FOR ABRUSOSIDES (A-D).
*ABRUSOSIDES A-D ARE SELECTIVELY PARTITIONED INTO EXTRACT

FIG.2 STRUCTURE OF ABRUSOSIDES A-D AND ABRUSOGENIN.
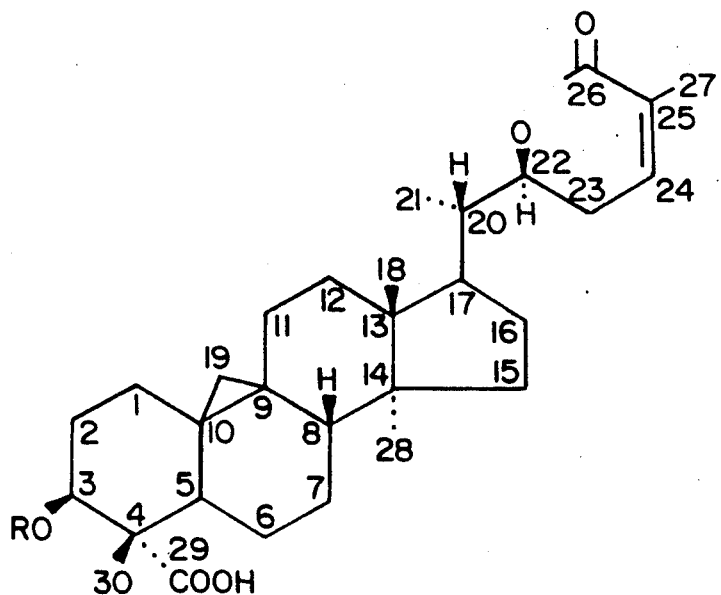
ABRUSOGENIN (R=H)
ABRUSOSIDE A (R=β-glc)
ABRUSOSIDE B (R=β-glcA-6-methyl ester$^2$-β-glc)
ABRUSOSIDE C (R=β-glc$^2$-β-glc)
ABRUSOSIDE D (R=β-glcA$^2$-β-glc)
FIG.3 STRUCTURE OF GLYCYRRHIZIN.
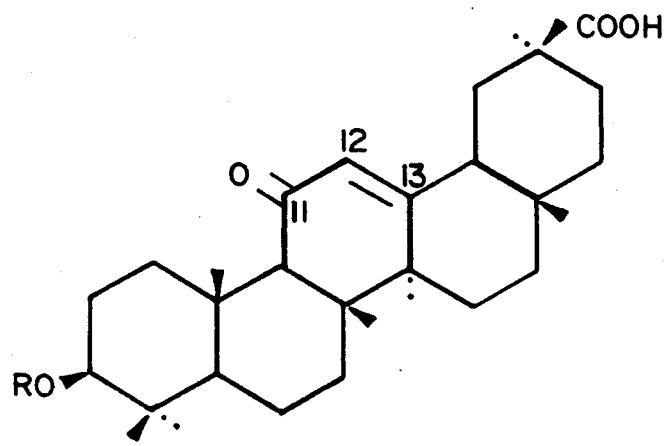
GLYCYRRHIZIN (R=β-glcA$^2$-β-glcA)
glc = GLUCOPYRANOSYL; glcA = GLUCURONOPYRANOSYL

ABRUSOSIDE A

ABRUSOSIDE B

ABRUSOSIDE C

ABRUSOSIDE D

NATURAL INTENSE SWEETENERS

This invention was made with Government support under 1 RO3 DE-07560-01 awarded by the National Institutes of Health. The Government has certain rights in the invention.

FIELD OF THE INVENTION

The present invention relates to novel sweet compounds derived from the genus Abrus, and their use as sweeteners. In particular, the present invention contemplates novel sweet compounds isolated from *A. precatorius* or *A. fruticulosus* and particularly, Abrusosides A, B, C and D and related compounds. The present invention also contemplates the use of these abrusosides and related compounds as sugar substitutes. The present invention contemplates the particular use of Abrusosides A-D as individual components or in mixtures in a method for sweetening comestibles, foodstuffs, beverages and medicinal agents

BACKGROUND OF THE INVENTION

Naturally occurring carbohydrate (i.e. sugar) sweeteners such as sucrose are still the most widely used sweetening agents. Sucrose is paramount among sweet compounds in that it produces sweetness that is unmasked by any other taste sensation. However, relatively large amounts of sucrose are used in sweetened foods, beverages, and medicines, and it is now accepted that sucrose is the main dietary source of dental caries in developed countries. While these naturally occurring carbohydrates generally fulfill the requirements of sweet taste, the abundant usage thereof does not occur without deleterious consequences such as high caloric intake and nutritional imbalance. In fact, often the level of these sweeteners required in foodstuffs is far greater than the level of the sweetener that is desired for economic, dietetic or other financial consideration. Therefore, there is much interest in discovering sugar substitutes that are highly sweet, and are also noncariogenic, noncaloric, nontoxic, and nonmutagenic, and exhibit acceptable taste characteristics, and solubility and stability profiles.

At the present time, only saccharin, aspartame, and acesulfame K are currently approved as intensely sweet sucrose substitutes in the United States and questions have been raised about the suitability of all of these substances. For example, many of these artificial sweeteners have the disadvantages of high cost, as well as delay in the perception of the sweet taste, persistent lingering of the sweet taste, and very objectionable bitter, metallic aftertaste when used in food products.

However, plants represent an alternative resource pool for the isolation and development of new high-intensity sweetening agents, and about 15 compound classes of plant-derived "natural" sweeteners are now known. In Japan, the natural sweeteners glycyrrhizin, stevioside, and thaumatin are all used as approved sucrose substitutes in the diet, while in the United Stated there is much public demand for natural substances, and much effort is currently being expended in the quest for additional naturally occurring sweeteners.

The plant genus Abrus belongs to the legume subfamily, Papilionoideae, which is constituted by up to 12 tropical species. One of the most widely distributed species in the genus, *Abrus precatorius* L. is native to India, and is also found in tropical and subtropical regions of Africa, Southeast Asia, Florida, Hawaii, and the West Indies. The plant is a vine that has leaves up to 4 inches long, and has many common names, including "Indian licorice", "Jamaica licorice", and "wild licorice". While the bright red seeds of *A. precatorius* are poisonous, the roots and leaves evidence no toxicity, and have a long history of human internal consumption, particularly as a licorice substitute. (Licorice is the source of the sweet triterpene glycoside, glycyrrhizin.) The leaves of *A. precatorius* have been found to be sweeter than the roots, and the presence of glycyrrhizin had been previously claimed by several authors to account for the sweetness of the leaves, in levels of as much as 9%. See, e.g., Hooper, *Pharm. J. Trans. Third Ser.* 24: 937-938, 1894; Akinloye, et al., *Nigerian J. Pharm.*, 12:405, 1981. Another species in this genus is *Abrus fruticulosus* which can also be found in Africa and Southeast Asia. The roots of this species have been used to treat digestive disorders.

The present invention reveals the presence of a new class of triterpene glycosides, the abrusosides, and in particular abrusosides A, B, C and D which are found in the genus Abrus. More specifically, these abrusosides can be isolated from *A. precatorius* and *A. fruticulosus*. All of these abrusosides are based on the aglycone, abrusogenin, which exhibits a unique carbon skeleton, not found in nature or derived synthetically to date. The sweetness of the genus Abrus (more specifically, *A. precatorius* and *A. fruticulosus*) can be ascribed solely to the abrusosides.

The present invention relates to the use of Abrusosides A-D as sugar substitutes and in particular, contemplates utilizing these abrusosides as replacements for sugars and other known natural sweeteners or sugar substitutes such as glycyrrhizin, stevioside, thaumatin, as well as the synthetic sweeteners, saccharin, aspartame, and acesulfame K.

Glycyrrhizin, for example, which has been used in various forms as a sweetener (i.e., ammoniated glycyrrhizin, glycyrrhizin, and its salt), has known adrenocorticomimetic activity (i.e., it mimics the effects of the adrenal cortex) which can cause abnormal retention of sodium, chlorine and water in humans, and this tends to limit the amount of the latter compounds that can be consumed. The abrusosides of the present invention do not exhibit these limitations.

The production of the abrusosides of the present invention can further be economically competitive with the production of other natural sugar substitutes.

SUMMARY OF THE INVENTION

Accordingly, one object of the present invention is to provide a new class of sweetening and flavor enhancing agents.

Another object of the present invention is to provide a new class of pharmaceutical compositions or medicinal agents.

A further object is to provide a new class of sugar substitutes which are safe and overcome the disadvantages of those products presently on the market.

Still another object of the present invention is to provide a sweetening and flavor enhancing agent which is a sugar substitute which exhibits similar mouth feel in various foods to those formulated with sucrose or other sugars and is capable of being readily crystallizable for easy processing as a sugar substitute.

Another object of this invention is to provide sweetened comestible and medicinal products employing the abrusosides of the present invention.

Still another object of this invention is to provide artificially sweetened food compositions employing the abrusosides of the present invention.

A further object of this invention to provide a method of sweetening medicinal and food compositions employing the abrusosides of the present invention.

A still further object of this invention is to provide an improved method for sweetening and flavoring products which eliminates the disadvantages associated with conventional methods utilizing glycyrrhizin.

These and other objects of the present invention are achieved by the discovery of a new class of sweeteners, i.e., Abrusosides A, B, C, and D derived from the genus Abrus and related compounds which can be employed as sugar substitutes in all comestibles, foods and medicaments which conventionally employ sugar or sugar substitutes such as saccharin and aspartame.

BRIEF DESCRIPTION OF THE DRAWINGS

FIG. 1 is a schematic representation of a solvent and purification scheme for isolating Abrusosides A-D from *Abrus precatorius* leaves.

FIG. 2 is a representation of the structure of the aglycone skeleton, abrusogenin, and abrusosides A-D.

FIG. 3 is a respresentation of the structure of glycyrrhizin.

DETAILED DESCRIPTION OF THE INVENTION

The present invention contemplates the discovery of a heretofore unknown group of natural intensely sweet compounds and their use as sugar substitutes. In particular, the present invention contemplates the use of Abrusosides A, B, C and D and related compounds as individual components or in mixtures for commercial use as medicinal agents, sweetening agents and flavor-enhancing agents in the food industry and the pharmaceutical industry.

Abrusosides A, B, C and D are four triterpene glycosides, based on a common aglycone, abrusogenin. These abrusosides are constituents of Abrus, for example, of *Abrus precatorius* leaves or from *A. fruticulosus*. For example, these constituents can be isolated from *A. precatorius* leaves according to the solvent extraction and partition scheme shown in FIG. 1.

The plant material derived from *A. precatorius* can be extracted with methanol, then partitioned with methanol, then partitioned between water and diethyl ether. The water extract can then be partitioned between 1-butanol and water. The first butanol extract (I) is saved and partitioned between 1-butanol and water. The second butanol extract (II) is discarded. The water extract is saved and partitioned between 1-butanol and water. The third butanol extract, containing the abrusosides A-D is purified by the addition of methanol. This results in the formation of a precipitate, removed by filtration leaving the mother liquor behind. Abrusoside D is isolated from this precipitate using droplet counter current chromatography. Abrusosides A-C are isolated from the mother liquor by purification via column chromatography. This same extraction and partition procedure can also be used with *A. fruticulosus*.

Figure 4A:
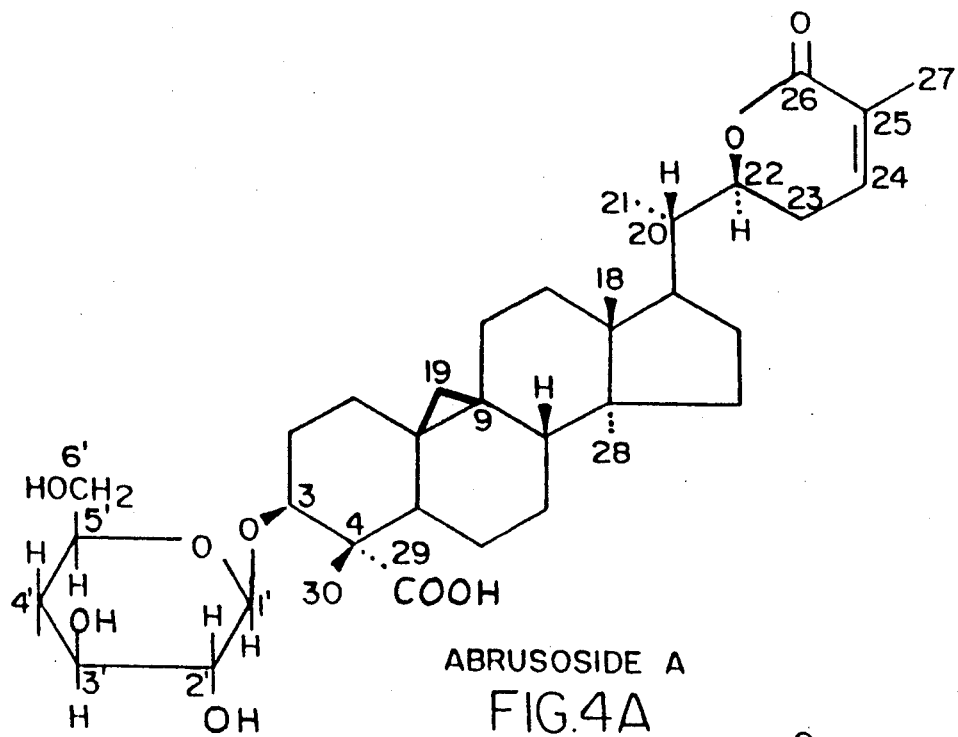
FIG. 4 is a representation of the complete structure of Abrusosides A-D.
Figure 4B:
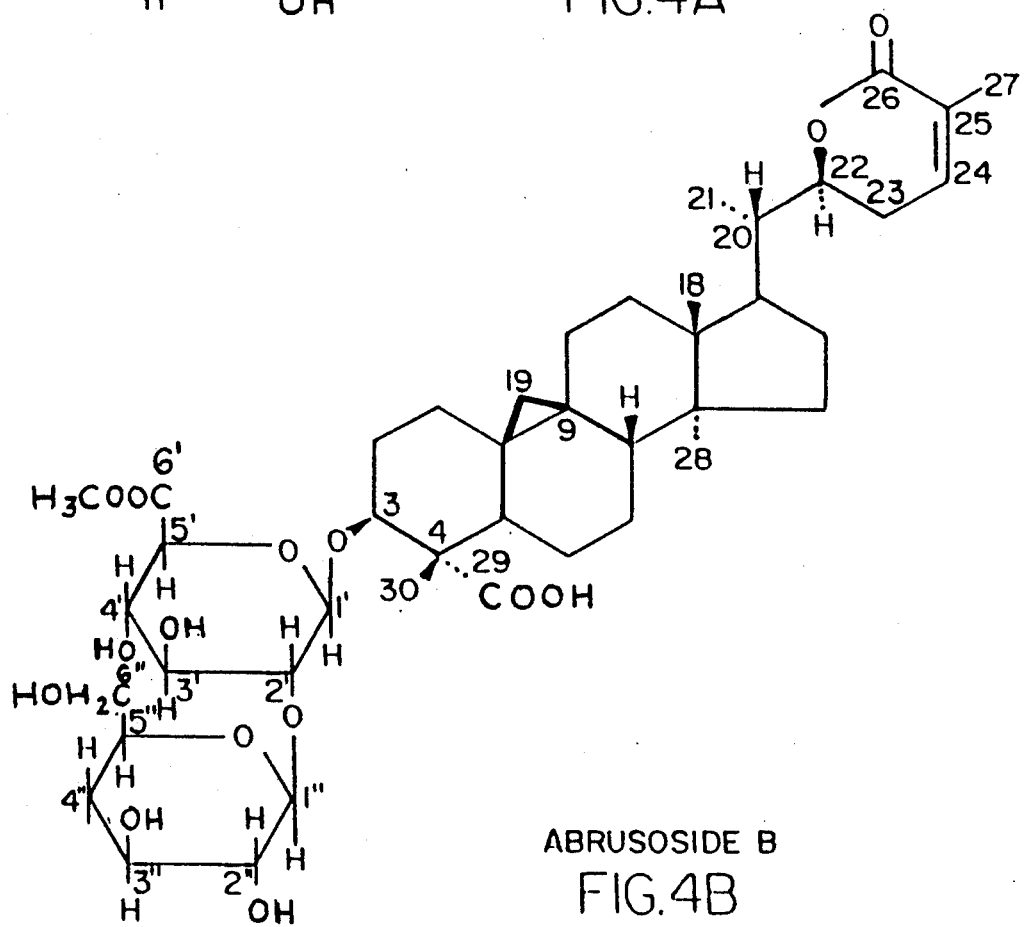
Figure 4C:
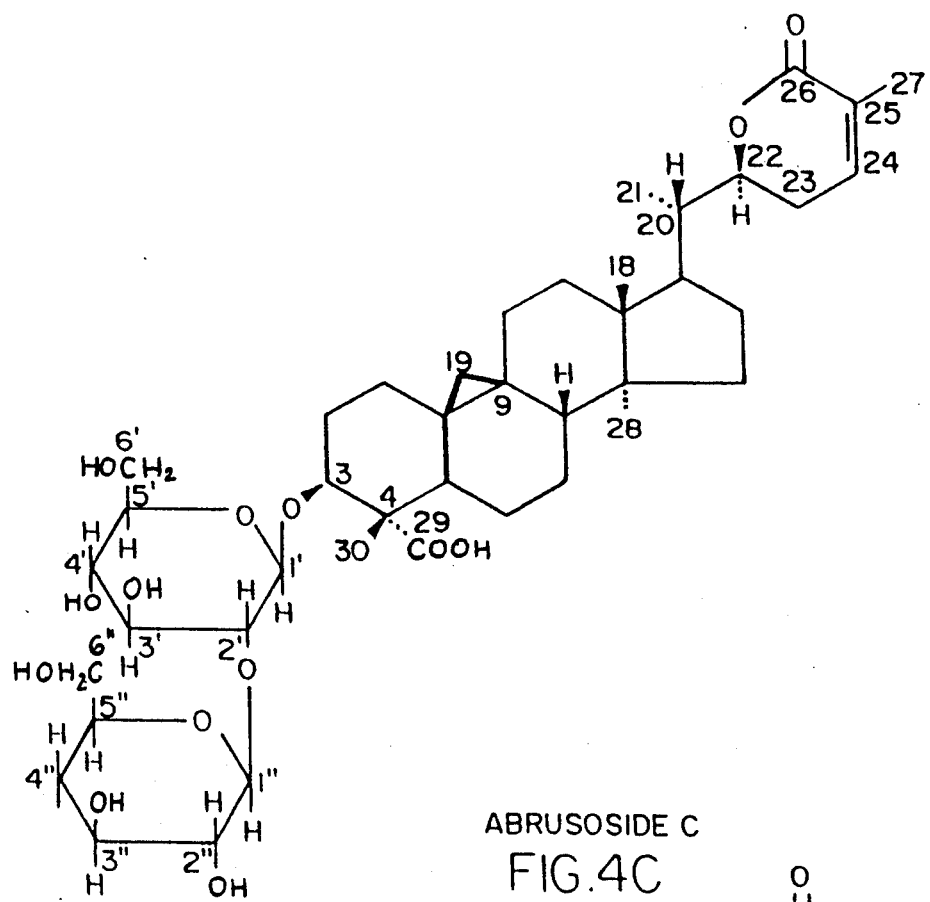
Figure 4D:
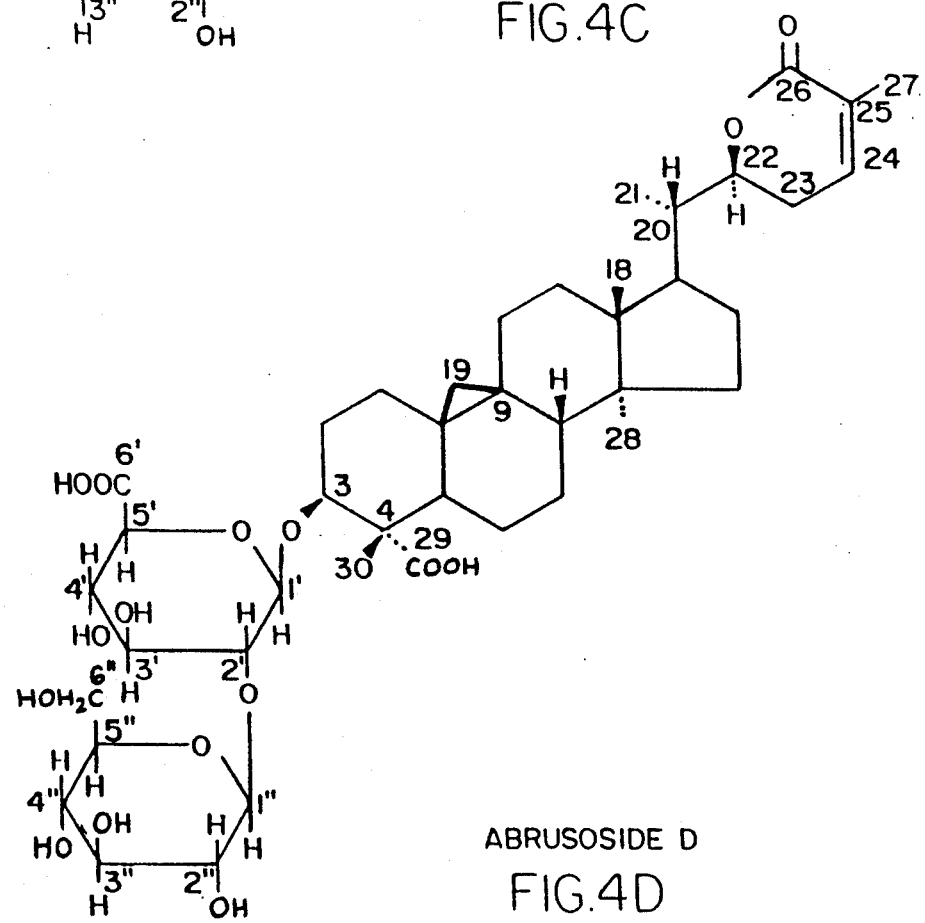

The structures of abrusosides A-D are shown in FIG. 2 and FIG. 4, and the structure of glycyrrhizin is shown in FIG. 3 for comparison purposes. The configurations and relative positions of the sugar moeities of Abrusoside A-D were established from the $^{13}$C-NMR data of the intact glycosides.

The abrusosides are found to be non-toxic in acute toxicity experiments, when administered to mice by oral incubation at a dose of 1 g/kg body weight, and are nonmutagenic when tested with *Salmonella typhimurium* strain TM677. When converted to their ammonium salts, abrusosides A, B, C, and D in water are rated by a human taste panel as possessing 30 x, 100 x, 50 x, and 75 x the sweetness of a 2% aqueous solution of sucrose, respectively. The compounds occurred in a combined yield of 0.389% w/w of the dried leaves of *A. precatorius*, and evidenced no instability during pH fluctuations from 3 to 10 used during their extraction. Abrusoside D is the most abundant of the abrusosides. In *Abrus fructiculosus*, abrusosides A-D occurred in a combined yield of 0.334% w/w.

In one embodiment, this invention contemplates substantially pure compounds of the formula (I)

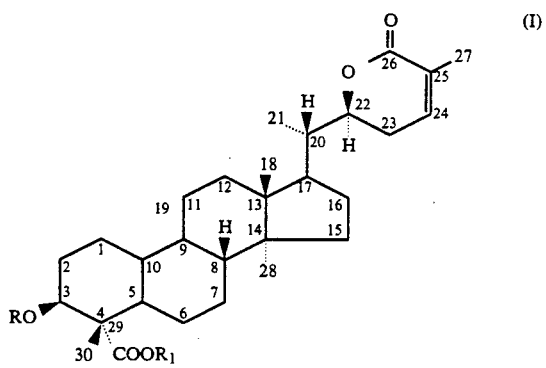

or salts thereof, wherein R represents at least one sugar unit and $R_1$ is H or lower alkyl. A sugar unit as defined in the specification and claims can be any of a class of sweet soluble crystalline carbohydrates, and, in particular, monosaccharides ($C_6H_{12}O_6$), disaccharides ($C_{12}H_{22}O_{11}$), trisaccharides ($C_{18}H_{32}O_{16}$) or tetrasaccharides ($C_{24}H_{42}O_{21}$), where the basic molecular formula of the saccharide is $C_6H_{12}O_6$. As defined herein, a dissacharide contains two $C_6H_{12}O_6$ units, a trisaccharide contains three $C_6H_{12}O_6$ units, and a tetrasaccharide contains four $C_6H_{12}O_6$ units. Examples of these sugar units include glucose, mannose, galactose, fructose, sucrose, lactose, maltose, raffinose, melezitose, laminaribiosyl, laminaritriosyl, and the like. These sugar units can be derivatized for example, with acids (COOH) or esters, i.e., carboxylic acid esters ($COOR_2$) or alcohol ester $$\left( \begin{array}{c} O \\ \parallel \\ OCR_2 \end{array} \right)$$

wherein $R_2$ is lower alkyl, with the preferred $R_2$ being $CH_3$. See for example, the sugar substitutes on Abrusoside B, or Abrusoside D, as depicted in FIG. 4 herein below.

The term lower alkyl as used herein refers to an alkyl chain containing from 1 to 6 carbon atoms. These groups may be straight chain or branched and include such groups as methyl, ethyl, propyl, isopropyl, butyl, sec-butyl, isobutyl, tert-butyl, amyl, hexyl, and the like.

A preferred embodiment of the present invention has the formula:

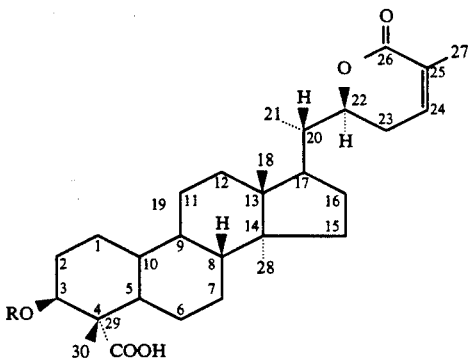

wherein R is H (abrusogenin), beta-glucopyranosyl (abrusoside A), beta-glucuronopyranosyl-6-methyl ester[2]-beta-glucopyranosyl (abrusoside B), beta-glucopyranosyl[2]-beta-glucopyranosyl (abrusoside C), beta-glucuronopyranosyl[12]-betaglucopyranosyl (abrusoside D).

The present invention also contemplates the insertion of one or more sugar units onto the aglycone skeleton. These related compounds to the isolated abrusosides can be prepared chemically, as shown by Nishizawa, et al., *Tetrahedron Letters*, 29: 4597–4598, 1988, and incorporated herein by reference, or enzymatically, as shown by Kusama, et al., *Agric. Biol. Chem.* 50: 2445–2451, 1986, also incorporated herein by reference.

The compounds of the present invention wherein $R_1$ is lower alkyl can be prepared from the corresponding acid ($R_1=H$) by art-recognized techniques. For example, compounds of Formula I wherein R is hydrogen can be reacted with lower alkanols ($R_2OH$) under Fischer esterification conditions.

Similarly, the esters of the derivatized sugar units can be prepared by art recognized techniques. The carboxylic acid esters can be prepared by reacting the corresponding acid with a lower alkanol ($R_2OH$) under Fischer esterified conditions. Similarly, the alcohol esters can be prepared by reacting the sugar unit with an acylating derivative of the formula

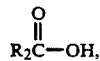

wherein $R_2$ is lower alkyl. For example, an acylating derivative may include acid chlorides, e.g.,

In any of these reactions, protection groups may be necessary. The protecting groups utilized are within the scope of one skilled in the art.

In another embodiment, the present invention contemplates using abrusosides A-D as a sugar substitute, and further, as a replacement for glycyrrhizin and other natural sucrose substitutes in their various forms. In particular, it is intended to use the abrusosides in the food industry. The compounds of the present invention can be added alone or with nontoxic carriers or other food ingredients such as acidulants, natural and artificial gums, bulking agents such as polycarbohydrates, dextrins, and other food approved carbohydrates and derivatives. Typical foodstuffs in which the sweetening agents of the present invention may be used are, for example, beverages including soft drinks, carbonated beverages, ready to mix beverages and the like, infused foods (e.g. vegetables or fruits), caramels, sauces, condiments, salad dressings, juices, chocolate or other flavored syrups, desserts, including puddings, gelatin and frozen desserts such as ice creams, sherbets, icings and flavored frozen desserts on sticks, confections, chewing gum, breathmints, cereals, baked goods, intermediate moisture foods (e.g., dog food) and the like. It is also contemplated to use the abrusosides in the pharmaceutical industry as a debittering agent in unpleasant tasting medicinal agents and can be applied to the flavoring of mouthwashes, aerosol breath deodorants, cough medicines, toothpaste, chewable vitamins and aspirin. Such a method of sweetening and enhancing the flavor of foodstuffs or medicinal agents comprises adding to said foodstuffs or medicinal agents a sweetening effective amount of a compound according to the present invention.

In order to achieve the effects of the present invention, the compounds described herein are generally added to the food product at a level which is effective to perceive sweetness in the foodstuff and suitably an amount in the range of from about 0.001 to about 0.5% by weight based on the consumed product. Greater amounts are operable but not practical. Generally, the sweetening effect provided by the present compounds are experienced over a wide pH range, e.g., 2 to 10, preferably 3 to 7, and in buffered and unbuffered formulations.

The present invention can also be used in hydrolyzed vegetable proteins, soy sauce, and bean paste, in order to modify the characteristic saltiness of these products. The present invention can further be utilized to modify the flavor of imitation meat products, derived from the controlled pyrolysis of sugars and amino acids.

In another embodiment of the present invention, a concentration range of from about 0.001 to about 0.5 wt % is contemplated for the sweetening agents of the present invention in solid compositions as described above. For liquid compositions as described above, a concentration range of from about 0.01 to about 0.50 grams per liter of aqueous solution is contemplated for the sweetening agents of the present invention.

The present compounds and pharmaceutical salts thereof can also be used as an antitussive, corrective agent, expectorant, and antiulcer agent. An advantage of the present invention is that it does not exhibit the harmful side effects of glycyrrhizin. More specifically, unlike glycyrrhizin, the compounds of the present invention do not produce edmea and hypertension. The functionality of the glycyrrhizin molecule that has been attributed to its toxic effects is the 11-oxo-12,13-dehydro group. No such unhindered enone moeity is present in the molecular structures of abrusosides A-D, and, therefore, these compounds may function as substitutes for glycyrrhizin, or when ammoniated, ammonium glycyrrhizin, without the liklihood of having harmful adrenocorticomimetic effects and therefore are contemplated as medicinal agents to be used in the same manner as described above for glycyrrhizin.

In a further embodiment of the present invention, a pharmaceutical composition is contemplated which contains an active ingredient of the present invention (i.e., abrusosides A-D, individually or in combination, or abrusogenin), in a convertible or pharmaceutically acceptable carrier wherein a concentration range of the active ingredient can be from about 0.001 to about 0.5 wt %.

The pharmaceutical composition containing the active ingredient of the present invention can be administered in a convenient manner such as by oral route.

The pharmaceutical composition may be orally administered, for example, with an inert diluent or with an assimilable edible carrier, or it may be compressed into tablets, or it may be incorporated directly with the food of the diet. For oral therapeutic administration, the pharmaceutical composition may be incorporated with excipients and used in the form of ingestible tablets, buccal tablets, troches, capsules, elixirs, suspensions, syrups, wafers, and the like. Such compositions and preparations should contain at least 0.001% of active ingredient.

Any material used in preparing any dosage unit form should be pharmaceutically pure and substantially nontoxic in the amounts employed. In addition, the active ingredient of the present invention (i.e., the abrusosides A-D) may be incorporated into sustained-release preparations and formulations.

As used herein, "pharmaceutically acceptable carrier" includes any and all solvents, dispersion media, coatings, antibacterial and antifungal agents, (e.g., parabens, chlorobutanol, phenol, sorbic acid, thimerosal and the like), isotonic (e.g., sugars or sodium chloride) absorption delaying agents, and the like, the use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

The principal active ingredient is used in effective amounts with a suitable pharmaceutically acceptable carrier in dosage unit form as hereinbefore disclosed. In the case of compositions containing supplementary active ingredients the dosages are determined by reference to the usual dose and manner of administration of the said ingredients.

The present invention also contemplates food acceptable salts as well as pharmaceutically acceptable compounds of Formula I. As used herein, these salts include the alkaline metal salts, such as sodium, potassium, lithium, the alkaline earth-metal salts, such as calcium, and magnesium and ammonium salts. The ammonium salts are the most preferred. These salts are prepared from the corresponding acids by art recognized techniques, e.g. by reacting compounds of Formula I with the corresponding basic salts, such as ammonium hydroxide, alkali hydroxides and the like.

The following examples are given for purely illustrative purposes of this invention without in any way limiting the same.

EXAMPLE I

1) ISOLATION AND PURIFICATION OF ABRUSOSIDES A-D FROM A. PRECATORIUS a) GENERAL PROCEDURES-Melting points are determined using a Kofler hot-stage instrument. Optical rotations are measured with a Perkin-Elmer 241 Polarimeter. The UV spectra are obtained on a Beckman DU-7 spectrometer and IR spectra measured on a Nicolet MX-1 FT-ir (KBr) interferometer. $^1$H-Nmr spectra are recorded with TMS as internal standard, employing either a Nicolet NT-360 or a Varian XL-300 instrument (360 MHz or 300 MHz, respectively). Low- and high-resolution mass spectra are obtained with a Varian MAT 112S instrument operating 70 eV. Gas chromatography/mass spectrometry (gc/ms) is performed on a Finnigan 4510 instrument, using a DB-1 column, between a temperature range of 120°–270° C., with the sugars derivatized as trimethylsilyl derivatives, and compared with authentic samples. Droplet counter-current chromatography (dccc) is performed on a Model-A instrument (Tokyo Rikakikai, Tokyo, Japan).

b) EXTRACTION AND FRACTIONATION-The air-dried plant material (600 g) is extracted with 80% v/v MeOH/$H_2O$, and gives 130 g of a dried MeOH/$H_2O$ extract on removal of solvent in vacuo. A portion of this residue (120 g) is partitioned between $H_2O$ (3 liters) and $Et_2O$ (4×1 liter), which yields 22.0 g of a dried Et20 extract that is discarded. The aqueous extract is further partitioned as shown in FIG. 1. Glycyrrhizin (Aldrich Chemical Co., Milwaukee, Wis.) is not detected by thin layer chromatography (tlc) in either the initial MeOH/$H_2O$ extract or butanol extract III.

When MeOH (100 ml) is added to butanol extract III (40 g), a precipitate is formed, and this precipitate is removed by filtration. Excess solvent is evaporated to afford 15 g of a MeOH-insoluble brown amorphous precipitate which is dried and later used for the isolation of abrusoside D. The mother liquor is also evaporated to yield 25 g of a residue which is purified by gel filtration by dissolving in MeOH (50 ml), with a 5-ml portion applied to the top of a glass column (1.9 cm × 50 cm) packed with Sephadex ® LH-20 (100 g) in MeOH. On elution with MeOH, a total of 300 fractions (100 drops each) are collected and monitored by tlc on silica gel G plates using $CHCl_3$-MeOH-$H_2O$ (65:35:10, lower phase, solvent 1) as the developing solvent. Fractions showing similar tlc profiles are pooled to give five combined fractions, inclusive of fractions 28–59 which appeared as a series of violet zones on tlc plates when visualized with vanillin-sulfuric acid spray reagent. This procedure is then repeated an additional nine times to afford a total of 10 g of dried residue.

c) ISOLATION OF ABRUSOSIDES A-C-Fractions 28–59 (10 g) are further fractionated by column chromatography (cc) by dissolution in 20 ml of solvent 1 and impregnation of solute on Si gel (20 g). The impregnated Si gel is applied to the top of a glass column (5 cm × 120 cm, Pirkle ® preparative column) packed with a slurry of Si gel (800 g, 230-400 mesh) in $CHCl_3$-MeOH (10:1). The column is eluted under low-pressure at a flow rate of 4.5 ml/min, using mixtures of $CHCl_3$-MeOH of increasing polarity. Altogether, 45 fractions (600 ml each) are collected and are monitored by tlc on Si gel G plates using solvent 1 and $CHCl_3$-MeOH-$H_2O$ (6:2:1, lower layer, solvent 2). Fractions showing similar tlc profiles are pooled to give 11 combined fractions.

Fraction 10 (0.52 g), which is eluted with CHCl$_3$-MeOH (100:15), is purified by repeated recrystallization in MeOH to afford abrusoside A (1, 180 mg, 0.033% w/w) as needle-shaped crystals. This isolate is shown to be homogeneous by tlc in three different solvent systems, namely, solvents 1 (R$_f$0.39), 2 (R$_f$0.14), and n-hexane-Et$_2$O-i-PrOH-EtOH-H$_2$O (6:16:9:10:9, upper layer, solvent 3, R$_f$ 0.57). Fraction 12 (0.51 g) is repeatedly treated with a CHCl$_3$-MeOH (1:1) mixture, and the purified precipitate is collected by filtration to yield the amorphous isolate, abrusoside B [2, 150 mg, 0.027% w/w), which is shown to be homogeneous by tlc in solvents 1-3 (R$_f$0.64, 0.43, and 0.47, respectively). Fractions 28-29 are also repeatedly treated with CHCl$_3$-MeOH (1:1), and collection of the purified precipitate afforded abrusoside C [220 mg, 0.040% w/w], which is shown to be pure by tlc in solvents 1-3 (R$_f$0.25, 0.06, and 0.50, respectively).

d) ISOLATION OF ABRUSOSIDE D-The precipitate (15 g) obtained by adding MeOH to BuOH extract III is further fractionated by dccc using an equilibrated mixture of CHCl$_3$-MeOH-n-PrOH-H$_2$O (6:4:1:5), with the upper phase employed as mobile phase. The solute (1.5 g) is dissolved in 5.0 ml mobile phase and on the addition of 5.0 ml of stationary phase, is introduced into a 10-ml sample chamber. Ascending development is employed at a pressure of 2-4 kg/cm$^2$. Fractions (300 drops each) are collected and monitored by tlc using solvents 1 and 2. This procedure is repeated once. Fractions 181-240 of each dccc run contained a compound shown to be pure by tlc in solvents 1 (R$_f$0.09), 3 (R$_f$ 0.30), and CHCl$_3$-MeOH-EtOH-40% v/v HOAc (8:3:3:2, solvent 4, R$_f$0.34), and are combined to yield abrusoside D (320 mg, 0.289% w/w).

e) CHARACTERIZATION OF ABRUSOSIDE A-This isolate exhibited the following data: mp 278°-280°; [α]$_D$ +11.2° (c 0.31, pyridine); uv, (EtOH) end absorption; ir, $_{max}$ (KBr) 3412 (OH), 1713 (C=O), 1127, 1076, 1045 cm$^{-1}$; $^1$H nmr, (360 MHz, C$_5$D$_5$N) δ6.58 (1H, m, H-24), 5.14 (1H, d, J=7.7 Hz, H-1'), 4.72 (1H, dd, J=11.7 Hz, J=4.3 Hz, H-3), 4.53 (2H, m, H-6', H-22), 4.40 (1H, dd, J=11.7 Hz, J=4.9 Hz, H-6'), 4.27 (2H, m, H-3', H-4'), 4.00 (2H, m, H-2', H-5'), 1.95 (3H, s, Me-27), 1.61 (3H, s, 30Me). 1.01 (3H, d, J=6.6 Hz, 21-Me), 0.95 (3H, s, 18-Me), 0.81 (3H, s, 28-Me), 0.57, 0.28 (2H, d, J=3.5 Hz, 19-H$_2$) ppm; $^{13}$C nmr, (90.8 MHz, C$_{67}$ D$_8$N) δ 180.19 (s, C-29), 166.34 (s, C-26), 140.71 (d, C-24), 127.65 (s, C-25), 105.50 (d, C-1'), 85.31 (d, C-3), 80.36 (d, C-22), 78.23 (d, C-5'), 77.95 (d, C-3'), 75.38 (d, C-2'), 71.40 (d, C-4'), 62.64 (t, C-6'), 54.39 (s, C-4), 48.98 (s, C-14), 48.02 (d, C-8), 47.83 (d, C-17), 45.30 (s, C-13), 44.70 (d, C-5), 40.04 (d, C-20), 35.50 (t, C-12), 32.93 (t, C-15), 31.79 (t, C-1), 29.73 (t, C-19), 29.29 (t, C-2), 27.87 (t, C-23), 27.49 (t, C-7), 26.44 (t, C-11), 25.84 (t, C-16), 25.51 (s, C-10), 23.10 (t, C-6), 19.78 (s, C-9), 19.46 (q, C-28), 18.00 (C-18), 17.28 (q, C-27), 13.11 (q, C-21), 11.08 (q, C-30) ppm; ei-ms, (70 eV) m/z 484 (M$^+$of aglycone, 1%), 469 (1), 466 (1), 448 (1), 423 (1), 405 (1), 385 (1), 367 (1), 345 (5), 327 (9), 314 (6), 299 (40), 281 (3), 175 (18), 159 (21), 147 (24), 133 (31); 121 (41), 111 (30), 107 (48), 95 (100), 81 (40), 55 (54), 44 (89); fab-ms, (DTE/DTT), m/z 669 [M+Na]$^+$; fab-ms, (LiI/3-NBA), m/z 653 [M+Li]$^+$; hr-fab-ms, mass measurement, found, 699.3608, calcd, for C$_{36}$H$_{54}$O$_{10}$Na, 699.3615.

Abrusoside A [30 mg] is hydrolyzed by treatment with 1 N HCl (8 ml) for 4 hr at 100° C., to produce an aglycone, abrusogenin [21 mg], which is recrystallized from MeOH as colorless, needle-shaped crystals, and is shown to be homogeneous by tlc in solvent 2 (R$_f$0.35), cyclohexaneEtOAc-CHCl$_3$-MeOH (6:4:2:3, solvent 5, R$_f$ 0.49), and CHCl$_3$-MeOH (10:1, solvent 6, R$_f$ 0.23). The H$_2$O layer containing the saccharide portion of abrusoside A is neutralized with silver carbonate, with the filtrate subjected to gc/ms and tlc, and found to contain only D-glucose. Abrusogenin exhibited the following data: mp 278°-280°; [α]$_D$+37° (c 0.1 CHCl$_3$-MeOH, 1:1), uv, (EtOH) end absorption; ir, ν$_{max}$ (KBr) 3430 (OH), 1707 (C=O), 1384, 1259, 1147, 1046 cm$^{-1}$; $^1$H nmr, (360 MHz, CDCl$_3$+CD$_3$OD) δ6.63 (1H, m, H-24), 4.50 (1H, dd, J=13.2 Hz, J=2.8 Hz, H-22), 4.09 (1H, dd, J=11.1 Hz, J=4.3 Hz, H-3), 2.58 (1H, m, H-23$_a$), 1.91 (3H, br. s, 27-Me), 1.13 (3H, s, 30Me), 1.00 (3H, d, J=6.7 Hz, 21-Me), 0.97 (3H, s, 18-Me), 0.93 (3H, s, 28-Me), 0.61, 0.39 (2H, d, J=4.0 Hz, 19-H$_2$) ppm; $^{13}$C nmr, (90.8 MHz, CDCl$_3$) δ 180.19 (s, C-29), 167.13 (s, C-26), 140.29 (d, C-24), 127.96 (s, C-25), 80.51 (d, C-22), 75.22 (d, C-3), 54.57 (s, C-4), 48.87 (s, C-14), 47.92 (d, C-8), 47.54 (d, C-17), 45.24 (s, C-13), 44.10 (d, C-5), 40.02 (d, C-20), 35.44 (t, C-12), 32.68 (t, C-15), 31.58 (t, C-1), 29.92 (t, C-19), 29.21 (t, C-2), 27.86 (t, C-23), 27.58 (t, C-7), 26.37 (t, C-11), 25.60 (t, C-16), 25.09 (s, C-10), 23.00 (t, C-6), 19.95 (s, C-9), 19.37 (q, C-28), 17.89 (q, C-18), 17.07 (q, C-27), 12.85 (q, C-21), 9.18 (q, C-30) ppm; ei-ms, (70 eV) m/z 484 (M$^+$, 10%), 469 (M$^+$-Me, 16), 466 (M$^+$-H$_2$O, 19), 448 (17), 423 (11), 385 (19), 367 (11), 344 (10), 314 (81), 299 (18), 233 (28), 215 (22), 203 (15), 187 (28), 173 (38), 161 (44), 147 (52), 119 (59), 111 (58), 107 (81), 95 (100) 93 (67), 91 (38), 81 (50), 79 (32) 69 (24), 67 (25), 55 (80); hr-ms, mass measurement, found, 484.3189, (calcd. for C$_{30}$H$_{44}$O$_5$, 484.3186); 367.2630, (C$_{25}$H$_{35}$O$_2$, 367.2635); 314.2245, (C$_{21}$H$_{30}$O$_2$, 314.224); 181.1223, (C$_{11}$H$_{17}$O$_2$, 181.1227); 167.1072, (C$_{10}$H$_{15}$O$_2$, 167.1071); 139.0764, (C$_8$H$_{11}$O$_3$, 139.0768); 111.0445, (C$_6$H$_7$O$_2$, 111.0445); 95.0131, (C$_5$H$_3$O$_2$, 95.0133).

Abrusogenin [10 mg] was methylated in ethereal diazomethane at room temperature overnight. On work-up, abrusogenin methyl ester [8 mg] was obtained as colorless prisms, after recrystallization in EtOAc, and was shown to be pure by tlc in solvents 3 (R$_f$0.71), 5 (R$_f$0.56), and 6 (R$_f$0.60). This derivative exhibited the following data: mp 246°-248°; [α]$_D$ +31.2° (c 0.08, CHCl$_3$-MeOH, 1:1); uv, (EtOH) end absorption; ir, ν$_{max}$ (KBr) 3529 (OH), 1710 (C=O), 1258, 1135, 1060, 1018 cm$^{-1}$, $^1$H nmr, (360 MHz, CDCl$_3$) δ 6.61 (1H, m, H-24), 4.50 (1H, dd, J=13.4 Hz, J=2.8 Hz, H-22), 4.10 (1H, dd, J=11.3 Hz, J=44 Hz, H-3), 3.71 (3H, s, 29-Ome), 2.57 (1H, m, H-23$_a$), 1.91 (3H, br. s, 27-Me), 1.15 (3H, s, 30-Me), 1.00 (3H, d, J=6.8 Hz, 21-Me), 0.96 (3H, s, 18-Me), 0.93 (3H, s, 28-Me), 0.61, 0.39 (2H, d, J=4.2 Hz, 19-H$_2$) ppm; $^{13}$C nmr, (90.8 MHz, CDCl$_3$) δ 177.42 (s, C-29), 166.56 (s, C-26), 139.65 (d, C-24), 128.12 (s, C-25), 80.21 (d, C-22), 75.32 (d, C-3), 54.80 (s, C-4) 51.85 (q, 29-CH$_3$), 48.79 (s, C-14), 47.85 (d, C-8), 47.42 (d, C-17), 45.20 (s, C-13), 44.30 (d, C-5), 40.05 (d, C-20), 35.40 (t, C-12), 32.58 (t, C-15), 31.43 (t, C-1), 29.88 (t, C-19), 27.85 (t, C-2), 27.85 (t, C-23), 27.55 (t, C-7), 26.32 (t, C-11), 25.52 (t, C-16), 25.04 (s, C-10), 23.07 (t, C-6), 19.91 (s, C-9), 19.38 (q, C-28), 17.86 (q, C-18), 17.14 (q, C-27), 12.82 (q, C-21), 9.26 (q, C-30) ppm; ei-ms, (70 ev) m/z 498 (M$^+$, 1%), 480 (M$^+$-OH, 3), 465 (1), 448 (4), 421 (1), 367 (3), 314 (22), 299 (6), 247 (11), 215 (14), 199 (11), 173 (30), 147 (42), 133 (55), 119 (60), 111 (68), 107 (76), 105 (68), 95 (100) 81(72), 67 (39), 55 (48).

Abrusogenin [10 mg] was acetylated at room temperature overnight in pyridine-(Ac)$_2$O (1.0 ml, 1:1). On work-up, the product abrusogenin 3-monoacetate [8 mg] was recrystallized as colorless needles from MeOH. This compound was shown to be homogeneous by tlc in three solvent systems (solvents 2, 5, and 6; R$_f$ 0.64, 0.43, and 0.47, respectively) and exhibited the following data; mp 308°-310°; [α]$_D$ +37.4° (c 0.06, CHCl$_3$-MeOH, 1:1); uv, (EtOH) end absorption; ir, $v_{max}$ (KBr) 1724 (C=O), 1703 (C=O), 1383, 1285, 1250, 1137 cm$^{-1}$; $^1$H nmr, (360 MHz, CDCl$_3$+CD$_3$OD) δ 6.66 (1H, m, H-24), 5.25 (1H, dd, J=11.5 Hz, J=4.3 Hz, H-3), 4.51 (1H, dd, J=12.6 Hz, J=2.4 Hz, H-22), 2.58 (1H, m, H-23$_a$), 2.01 (3H, s, —OAc), 1.91 (3H, br, s, 27-Me), 1.20 (3H, s, 30-Me), 1.00 (3H, d, J=6.7 Hz, 21-Me), 0.98 (3H, s, 18-Me), 0.94 (3H, s, 28-Me), 0.64, 0.42 (2H, d, J=4.1 Hz, 19-H$_2$) ppm; $^{13}$C nmr, (90.8 MHz, CDCl$_3$+CD$_3$OD) δ 178.51 (s, C-29), 170,79 (s, —OCOCH$_3$), 167.13 (s, C-26), 140.26 (d, C-24), 128.01 (s, C-25), 80.53 (d, C-22), 77.84 (d, C-3), 52.74 (s, C-4), 48.85 (s, C-14), 47.91 (d, C-8), 47.56 (d, C-17), 45.28 (s, C-13), 44.31 (d, C-5), 40.04 (d, C-20), 35.45 (t, C-12), 32.64 (t, C-15), 31.22 (t, C-1), 29.89 (t, C-19), 27.85 (t, C-23), 27.59 (t, C-7), 26.37 (t, C-11), 26.12 (t, C-2), 25.49 (t, C-16), 25.09 (s, C-10), 22.78 (t, C-6), 21.19 (q, —OCOCH$_3$), 20.17 (s, C-9), 19.36 (q, C-28), 17.91 (q, C-18), 17.07 (q, C-27), 12.98 (q, C-21), 10.34 (q, C-30) ppm; ei-ms, (70 eV) m/z 526 (m$^+$, 3%), 511 (3), 466 (M$^+$-OAc, 16), 448 (15), 427 (7), 405 (6), 367 (11), 314 (19), 299 (5), 233 (17), 215 (11), 187 (13), 173 (19), 159 (25), 147 (28), 121 (29), 119 (34), 111 (33), 107 (43), 105 (37), 133 (34), 95 (71), 81 (38), 67 (26), 55 (69), 43 (100).

f) CHARACTERIZATION OF ABRUSOSIDE B-Abrusoside B exhibited the following data: mp 243°-245°; [α]$_D$+5.8° (c 0.35, pyridine); uv, (EtOH) end absorption; ir, $v_{max}$ (KBr) 3407 (OH), 1712 (C=O), 1378, 1245, 1114, 1081, 1059 cm$^{-1}$; $^1$H nmr, (360 MHz, C$_5$D$_5$N) δ 6.56 (1H, m, H-24), 5.37 (1H, d, J=7.6 Hz, H-1"), 5.28 (1H, br. d, W$_{\frac{1}{2}}$=7.1 Hz, H-1'), 4.87 (dd, J=11.7 Hz, J=4.4 Hz, H-3), 3.86 (1 H, s, 6'-OMe), 1.94 (3H, br. s, 27-Me), 1.71 (3H, s, 30-Me), 1.01 (3H, d, J=6.5 Hz, 21-Me), 0.96 (3H, s, 18-Me), 0.81 (3H, s, 28-Me), 0.60, 0.30 (2H, d, J=3.5 Hz, 19-H$_2$) ppm; $^{13}$C nmr, (90.8 MHz, C$_5$D$_5$N) δ 179.52 (s, C-29), 170.35 (s, C-6'), 166.21 (s, C-26), 140.51 (d, C-24), 127.71 (s, C-25), 106.35 (d, C-1"), 102.47 (d, C-1'), 84.05 (d, C-2'), 82.59 (d, C-3), 80.28 (d, C-22), 78.15 (d, C-5"), 78.05 (d, C-5'), 77.70 (d, C-3'), 77.43 (d, C-3"), 76.15 (d, C-2"), 72.87 (d, C-4'), 71.32 (d, C-4"), 62.59 (t, C-6"), 54.16 (s, C-4), 51.99 (q, 6'-OCH$_3$), 48.93 (s, C-14), 48.03 (d, C-8, C-17), 45.32 (s, C-13), 45.19 (d, C-5), 40.07 (d, C-20), 35.58 (d, C-12), 32.96 (t, C-15), 31.88 (t, C-1), 29.73 (t, C-19), 29.63 (t, C-2), 27.88 (t, C-23), 27.52 (t, C-7), 26.41 (t, C-11), 25.97 (t, C-16), 25.39 (s, C-10), 23.21 (t, C-6), 19.77 (s, C-9), 19.48 (q, C-28), 18.10 (q, C-18), 17.28 (q, C-27), 13.11 (q, C-21), 10.60 (q, C-30) ppm; ei-ms, (70 eV) m/z 484 (M$^+$ of aglycone, 3%), 469 (3), 466 (4), 448 (5), 438 (3), 423 (3), 405 (2), 385 (4), 367 (4), 314 (14), 299 (4), 233 (6), 173 (14), 147 (13), 121 (18), 95 (33), 73 (20), 55 (38), 44 (100); fab-ms, (DTE/DTT), m/z 859 [M+Nz]$^+$; fab-ms, (3-NBA), m/z 837 [M+H]$^+$, 859 [M+Na]$^+$; fab-ms, (LiI/3-NBA), m/z 843 [M+Li]$^+$, 649 [M−H+2 Li]$^+$; hr-fab-ms, mass measurement, found, 837.4271, calcd, for C$_{43}$H$_{65}$O$_{16}$, 837.4273.

Abrusoside B [5 mg] was hydrolyzed with 1N HCl (3 ml) under the same conditions described for abrusoside A. On work-up, the resultant aglycone (2.8 mg) was shown to be identical to abrusogenin, by physical (mmp), spectral (ir $^1$H-nmr, ms), and tlc data comparison. On neutralization of the H$_2$O layer obtained from this hydrolysis, the sugars identified by gc/ms and tlc were D-glucose and D-glucuronic acid methyl ester. The latter compound was generated from the authentic D-glucuronic acid by methylation using diazomethane.

g) CHARACTERIZATION OF ABRUSOSIDE C-This abrusoside exhibited the following data: mp 260°-262°; [α]$_D$+31.4° (c 0.34, pyridine); uv, (EtOH) end absorption; ir, $v_{max}$ (KBr) 3412 (OH), 1709 (C=O), 1379, 1259, 1077 cm$^-$; $^1$H nmr, (360 MHz, C$_5$D$_5$N) δ 6.56 (1H, m, H-24), 5.23 (1H, d, J=7.7 Hz, H-1"), 5.15 (1H, d, J=7.6 Hz, H-1'), 4.70 (1H, dd, J=11.7 Hz, J=4.3 Hz, H-3), 1.94 (3H, br. s, 27-Me), 1.66 (3H, s, 30-Me), 1.01 (3H, d, J=6.6 Hz, 21-Me), 0.94 (3H, s, 18-Me), 0.79 (3H, s, 28-Me), 0.56, 0.28 (2H, d, J=3.4 Hz, 19-H$_2$) ppm; $^{13}$C nmr, (90.8 MHz, C$_5$D$_5$N) δ 178.86 (d, C-29), 165.83 (s, C-26), 139.97 (d, C-24), 128.10 (s, C-25), 105.80 (d, C-1"), 103.63 (d, C-1'), 84.96 (d, C-3), 83.88 (d, C-2"), 80.45 (d, C-22), 78.34 (d, C-3"), 78.03 (d, C-5', C-5"), 77.59 (d, C-3'), 76.60 (d, C-2"), 71.84 (d, C-4"), 71.25 (d, C-4'), 63.16 (t, C-6"), 62.62 (t, C-6'), 54.49 (s, C-4), 49.17 (s, C-14), 48.36 (d, C-8), 47.68 (d, C-17), 45.71 (s, C-13), 44.92 (d, C-5), 40.34 (d, C-20), 35.67 (t, C-12), 33.27 (t, C-15), 31.98 (t, C-1), 29,63 (t, C-19), 29.56 (t, C-2), 28.09 (t, C-23), 27.62 (t, C-7), 26.79 (t, C-11), 25.87 (s, C-16), 25.79 (t, C-10), 23.02 (t, C-6), 20.21 (s, C-9), 19.56 (q, C-28), 17.90 (q, C-18), 17.00 (q, C-27), 13.23 (q, C-21), 10.87 (q, C-30) ppm; ei-ms, (70 eV) m/z 484 (M$^+$ of aglycone, 2%), 469 (4), 466 (4), 448 (4), 423 (3), 405 (3), 385 (5), 367 (3), 314 (18), 299(5), 255 (1), 233 (6), 173 (24), 145 (23), 133 (22), 119 (21), 111 (23), 107 (31), 105 (23), 95 (62), 73 (76), 54 (72), 43 (100); fab-ms, (DTE/DTT), m/z 831 [M+Na]$^+$; fab-ms, (LiI/3-NBA), m/z 815 [M+Li]$^+$, 821 [M−H+2 Li]$^+$; hr-fab-ms, mass measurement, f,und, 815.4406, calcd, for C$_{42}$H$_{64}$O$_{15}$Li, 815.4408.

Abrusoside C [5 mg] was acid hydrolyzed and worked up by the method described for abrusoside A. The aglycone obtained was identical to abrusogenin by mmp, ir, $^1$H-nmr, ms, and co-tlc, and only D-glucose was detected by gc/ms and tlc.

h) CHARACTERIZATION OF ABRUSOSIDE D-Abrusoside D exhibited the following data: mp 237°-239°; [α]$_D$+9.9° (c 0.31 pyridine); uv, (EtOH), end absorption; ir, $v_{max}$ (KBr) 3412 (OH), 1710 (C=O), 1379, 1258, 1115, 1077, 1054 cm$^{-1}$; $^1$H nmr (360 MHz, C$_5$D$_5$N) δ 6.56 (1H, m, H-24), 5.44 (1H, d, J=7.4 Hz, H-1'), 5.22 (1H, d, J=7.2 Hz, H-1"), 4.83 (1H, dd, J=11.7 Hz, J=4.0 Hz, H-3), 4.74 (1H, d, J=10 Hz, H-5'), 1.94 (3H, br. s, 27-Me), 1.70 (3H, s, 30-Me), 1.01 (3H, d, J=6.6 Hz, 21-Me), 0.92 (3H, s, 18-Me), 0.78 (3H, s, 28-Me), 0.50, 0.23 (2H, d, J=3.5 Hz, 19-H$_2$) ppm; $^{13}$C nmr, (90.8 MHz, C$_5$D$_5$N) δ 179.54 (s, C-29), 173.69 (s, C-6'), 166.21 (s, C-26), 140.58 (d, C-24), 127.68 (s, C-25), 105.77 (d, C-1"), 102.59 (d, C-1'), 83.71 (d, C-3), 83.08 (d, C-2'), 80.29 (d, C-22), 78.07 (d, C-3", C-5"), 77.70 (d, C-5'), 77.30 (d, C-3'), 76.52 (d, C-2"), 73.19 (d, C-4'), 71.29 (d, C-4"), 62.56 (t, C-6"), 54.18 (s, C-4), 48.91 (s, C-14), 48.03 (d, C-8), 47.92 (d, C-17), 45.30 (s, C-13), 44.86 (d, C-5), 40.06 (d, C-20), 35.52 (t, C-12), 32.39 (t, C-15), 31.79 (t, C-1), 29.71 (t, C-19), 29.23 (t, C-2), 27.89 (t, C-23), 27.50 (t, C-7), 26.39 (t, C-11), 25.86 (t, C-16), 25.44 (t, C-10), 23.12 (t, C-6), 19.78(t, C-9), 19.47 (q, C-28), 18.04 (q, C-18), 17.29 (q, C-27), 13.12 (q, C-21), 11.00 (q, C-30) ppm; ei-ms, (70 eV) m/z 469 (M$^+$ of aglycone-Me, 1%), 448 (2), 423 (1), 405 (2), 385 (1), 367 (2), 314 (8), 299 (2), 233 (5), 173 (15), 145 (17), 119 (20), 95 (36), 73 (34), 44 (100); fab-ms, (DTT/DTE), m/z 823 [M+H]+, 845 [M+Na]+; hr-fab-ms, mass measurement, found, 823.4123, calcd for $C_{42}H_{63}O_{16}$, 823.4116.

When abrusoside D [4, 7 mg] was acid hydrolyzed as described for abrusoside A [1], abrusogenin [5, 2.9 mg] (mmp, ir, $^1H$ nmr, ms, co-tlc) and D-glucose and D-glucuronic acid (gc/ms, tlc) were the products identified.

2) PRELIMINARY SAFETY STUDIES ON ABRUSOSIDES A-D

A. Acute Toxicity Studies in Mice

The sweet isolates, abrusosides A-D, are each tested for acute toxicity in mice. Experiments are carried out with male Swiss-Webster mice (6-8 weeks old), that are housed in temperature-controlled rooms with a 12-hr light/dark cycle, and allowed free access to water and food. After acclimatization for three days, groups of 10 animals receive a single 1 g/kg body weight dose of either abrusoside A, B, C, or D by oral intubation. Test materials are suspended in 1% aqueous sodium carboxymethylcellulose. A control group treated with only 1% sodium caroboxymethylcellulose is also included in the experiment. In all experiments, no incidence of mortality occurred for up to 14 days after dosing. Animals are examined for body weight variations on days 0 (prior to administration), 1, 3, 7, and 14. Body weight variations between treated and control groups are analyzed by one-way analysis of variance using an appropriate computer program. Results of acute toxicity assays for abrusosides A and B, and for abrusosides C and D, are shown in Tables 1 and 2, respectively. It may be seen from these tables that no significant differences in body weight variation occurred between each of the four test compounds and the controls, when assessed for a fourteen day period following compound administration.

TABLE 1

Results of Acute Toxicity Assays on Abrusosides A and B Utilizing Male Swiss-Webster Mice[a,b]

| Dose (g/kg) | Average body weight (g) of test animals at time intervals | | | | |
|---|---|---|---|---|---|
| | Day 0 | Day 1 | Day 3 | Day 7 | Day 14 |
| Abrusoside A | | | | | |
| 0 | 23.3 ± 1.4 | 23.6 ± 1.4 | 24.1 ± 1.5 | 25.4 ± 2.0 | 26.1 ± 1.9 |
| 1 | 23.4 ± 1.4 | 23.7 ± 1.2 | 24.4 ± 1.5 | 25.4 ± 1.3 | 26.1 ± 2.3 |
| t | (0.292) | (0.153) | (0.368) | (0.000) | (0.000) |
| Abrusoside B | | | | | |
| 0 | 23.3 ± 1.4 | 23.6 ± 1.4 | 24.1 ± 1.5 | 25.4 ± 2.0 | 26.1 ± 1.9 |
| 1 | 23.5 ± 1.0 | 23.7 ± 1.0 | 23.9 ± 1.1 | 25.0 ± 1.3 | 26.4 ± 1.7 |
| t | (0.432) | (0.330) | (0.458) | (0.576) | (0.282) |

[a]Isolates were dispersed in 1% sodium carboxymethylcellulose (CMC) and mice in each test group were dosed by oral intubation at 1 g/kg body weight. Animals in the control group were treated with 1% CMC only.
[b]The test t method was used to analyze these results for any significant variation; therefore, there was no significant difference between the test and control groups (0.95 confidence).

TABLE 2

Results of Acute Toxicity Assays on Abrusosides C and D Utilizing Male Swiss-Webster Mice[a,b]

| Dose (g/kg) | Average body weight (g) of test animals at time intervals | | | | |
|---|---|---|---|---|---|
| | Day 0 | Day 1 | Day 3 | Day 7 | Day 14 |
| Abrusoside C | | | | | |
| 0 | 23.3 ± 1.4 | 23.6 ± 1.4 | 24.1 ± 1.5 | 25.4 ± 2.0 | 26.1 ± 1.9 |
| 1 | 23.4 ± 1.3 | 23.8 ± 1.1 | 24.3 ± 1.2 | 25.3 ± 1.4 | 26.9 ± 1.6 |
| t | (0.282) | (0.371) | (0.302) | (0.129) | (0.930) |
| Abrusoside D | | | | | |
| 0 | 23.3 ± 1.4 | 23.6 ± 1.4 | 24.1 ± 1.5 | 25.4 ± 2.0 | 26.1 ± 1.9 |
| 1 | 24.1 ± 1.8 | 24.4 ± 1.7 | 24.9 ± 1.8 | 25.7 ± 2.1 | 27.0 ± 2.9 |
| t | (1.199) | (1.140) | (0.991) | (0.383) | (0.812) |

[a]Isolates were dispersed in 1% sodium carboxymethylcellulose (CMC) and mice in each test group were dosed by oral intubation at 1 g/kg body weight. Animals in the control group were treated with 1% CMC only.
[b]The test t method was used to analyze these results for any significant variation; therefore, there was no significant difference between the test and control groups (0.95 confidence).

B. Mutagenicity Studies Using Bacteria

*Salmonella typhimurium* strain TM677, carrying the "R-factor" plasmid pKM101, is used for the assessment of mutagenic activity. Mutagenic assays are conducted on abrusosides A, B, C, and D, both in the absence and presence of a metabolic activating agent, obtained from a 9,000 × g supernatant fraction from the livers of Aroclor 254-pretreated rats. The following protocols are used in this procedure.

1. Treatment of animals and isolation of the 9,000 × g supernatant

Male Sprague-Dawley rats (body weight 100-120 g) were housed in air-conditioned quarters, with a 12 hr/12 hr light-dark cycle, and are given food and water ad libitum. The rats (groups of 10) are given single intraperitoneal injections of Aroclor 1254 (400 mg/kg) in corn oil. Four days after the treatment with Aroclor 1254, the rats are sacrificed by decapitation. Their livers are immediately excised, rinsed several times with cold 0.14 M NaCl, minced, and homogenized with 3 volumes (v/w) of 50 mM Tris HCl, pH 5, containing 0.14 M KCl, using a glass homogenizing vessel and a motor-driven Teflon pestle. The homogenate is filtered through cheese-cloth, and centrifuged at 9,000 g for 20 minutes to yield an S-9 fraction. The isolation procedures described above are conducted at 0°-4° C., and the isolated S-9 fraction is stored in small aliquots in liquid nitrogen.

2. Bacterial mutagenesis assay

Duplicate 0.98-ml reaction mixtures containing 0.1 mg of NADP+, 1.0 mg of glucose-6-phosphate, 0.8 units of glucose-6-phosphate dehydrogenase, 0.67 mg of $MgCl_2$, the S-9 fraction, and approximately $7 \times 10^6$ bacteria in logarithmic phase, are prepared in minimal essential medium. When metabolic activation is not required, only bacteria and minimal essential medium are mixed.

After addition of each test substance dissolved in 20 ul of DMSO, the mixtures are slowly rotated at 37° C. for 2 hours. Each reaction mixture is then quenched by addition of 4 ml phosphate-buffered saline. The bacteria are recovered by centrifugation, resuspended, diluted as appropriate, and plated, in triplicate, in the presence or absence of 8-azaguanine. Plates are scored after a number of colonies observed on plates containing 8-azaguanine divided by the average number of plates not containing azaguanine, after correcting for dilution factors. The latter value is used to define the percentage of bacteria surviving the treatment, relative to a control in which only an equivalent amount of solvent had been added.

The spontaneous mutant fraction for this assay is $7.4 \pm 5 \times 10^{-5}$ (n=145). A compound is said to cause significant mutation if the induced mutant fraction is greater than or equal to two times the spontaneous mutant fraction.

The sweet isolates, abrusosides A-D, are evaluated as non-mutagenic for *Salmonella typhimurium* strain TM677, both in the absence and presence of an S-9 metabolic activating system, as shown in Tables 3-6, respectively.

TABLE 3

Results of Forward Mutation Assays on Abrusoside A Utilizing *Salmonella typhimurium* Strain TM677[a]

| Compound Added | Concentration (mg/ml) | Solvent | Activating System | Mutant Fraction ($\times 10^5$) | % Survival |
|---|---|---|---|---|---|
| none | — | DMSO | none | 9.6 | 100 |
| Abrusoside A | 2.5 | DMSO | none | 7.9 | 100 |
|  | 5.0 |  |  | 8.1 | 100 |
| none | — | DMSO | Aroclor S-9 | 7.6 | 100 |
| Abrusoside A | 2.5 | DMSO | Aroclor S-9 | 8.1 | 100 |
|  | 5.0 |  |  | 7.3 | 100 |

[a]Each compound was assayed in duplicate at the indicated concentration. Each duplicate was placed in triplicate, both in the presence and absence of 8-azaguanine (8-AG), and the data were averaged. The spontaneous mutant fraction (i.e., average number of clones on 8-AG plates/average number of clones on plates without 8-AG) for this assay is $7.4 \pm 5 \times 10^5$ (n = 145). A compound is said to cause significant mutation if the induced mutant fraction is greater than or equal to two times the spontaneous mutant fraction.

TABLE 4

Results of Forward Mutation Assays on Abrusoside B Utilizing *Salmonella typhimurium* Strain TM677[a]

| Compound Added | Concentration (mg/ml) | Solvent | Activating System | Mutant Fraction ($\times 10^5$) | % Survival |
|---|---|---|---|---|---|
| none | — | DMSO | none | 9.6 | 100 |
| Abrusoside B | 2.5 | DMSO | none | 8.7 | 100 |
|  | 5.0 |  |  | 7.3 | 100 |
| none | — | DMSO | Aroclor S-9 | 7.6 | 100 |
| Abrusoside B | 2.5 | DMSO | Aroclor S-9 | 7.2 | 100 |
|  | 5.0 |  |  | 8.2 | 100 |

[a]Each compound was assayed in duplicate at the indicated concentration. Each duplicate was placed in triplicate, both in the presence and absence of 8-azaguanine (8-AG), and the data were averaged. The spontaneous mutant fraction (i.e., average number of clones on 8-AG plates/average number of clones on plates without 8-AG) for this assay is $7.4 \pm 5 \times 10^5$ (n = 145). A compound is said to cause significant mutation if the induced mutant fraction is greater than or equal to two times the spontaneous mutant fraction.

TABLE 5

Results of Forward Mutation Assays on Abrusoside C Utilizing *Salmonella typhimurium* Strain TM677[a]

| Compound Added | Concentration (mg/ml) | Solvent | Activating System | Mutant Fraction ($\times 10^5$) | % Survival |
|---|---|---|---|---|---|
| none | — | DMSO | none | 9.6 | 100 |
| Abrusoside C | 2.5 | DMSO | none | 8.1 | 100 |
|  | 5.0 |  |  | 7.6 | 100 |
| none | — | DMSO | Aroclor S-9 | 7.6 | 100 |
| Abrusoside C | 2.5 | DMSO | Aroclor S-9 | 7.7 | 100 |
|  | 5.0 |  |  | 6.7 | 100 |

[a]Each compound was assayed in duplicate at the indicated concentration. Each duplicate was placed in triplicate, both in the presence and absence of 8-azaguanine (8-AG), and the data were averaged. The spontaneous mutant fraction (i.e., average number of clones on 8-AG plates/average number of clones on plates without 8-AG) for this assay is $7.4 \pm 5 \times 10^5$ (n = 145). A compound is said to cause significant mutation if the induced mutant fraction is greater than or equal to two times the spontaneous mutant fraction.

TABLE 6

Results of Forward Mutation Assays on Abrusoside D Utilizing *Salmonella typhimurium* Strain TM677[a]

| Compound Added | Concentration (mg/ml) | Solvent | Activating System | Mutant Fraction ($\times 10^5$) | % Survival |
|---|---|---|---|---|---|
| none | — | DMSO | none | 16.5 | 100 |
| Abrusoside D | 2.5 | DMSO | none | 16.7 | 100 |
|  | 5.0 |  |  | 15.3 | 100 |
| none | — | DMSO | Aroclor S-9 | 11.3 | 100 |
| Abrusoside D | 2.5 | DMSO | Aroclor S-9 | 11.8 | 100 |
|  | 5.0 |  |  | 11.0 | 100 |

[a]Each compound was assayed in duplicate at the indicated concentration. Each duplicate was placed in triplicate, both in the presence and absence of 8-azaguanine (8-AG), and the data were averaged. The spontaneous mutant fraction (i.e., average number of clones on 8-AG plates/average number of clones on plates without 8-AG) for this assay is $7.4 \pm 5 \times 10^5$ (n = 145). A compound is said to cause significant mutation if the induced mutant fraction is greater than or equal to two times the spontaneous mutant fraction.

3) SENSORY EVALUATION OF ABRUSOSIDES A-D

After demonstrating that the isolates, abrusosides A-D, are innocuous (nontoxic) in preliminary safety testing, these compounds are tasted by a human panel. Abrusoside A (4 mg) is dissolved in 0.033N ammonium hydroxide solution (0.2 ml), to which is added 1.8 ml of water to yield the equivalent of a 0.2 % w/v solution of abrusoside A. Aliquots (0.2 ml) of this solution are diluted with 0.4, 0.8, 1.3, and 1.8 ml water, respectively. The diluted solutions is tasted sequentially, in order to judge the intensity of sweetness equivalent to that of a 2% w/v aqueous sucrose solution. Similar procedures are used in the sensory evaluation of abrusosides B-C, expect that the concentrations of the ammonium hydroxide solutions used are 0.05N for abrusosides B and C, and 0.025N for abrusoside D. These sensory experiments are performed by a small panel consisting of three persons.

Abrusosides A-D are rated as being 30, 100, 50, and 75 times sweeter than 2% sucrose respectively. When tested at a concentration level of 0.04% w/v, abrusoside D showed a lingering sweetness lasting about 30 minutes. All four compounds appear to show a delayed onset in perception of their sweetness (5 to 30 seconds).

EXAMPLE II

ISOLATION AND PURIFICATION OF ABRUSOSIDES A-D FROM A. FRUTICULOSUS

Preliminary thin-layer chromatographic (TLC) analysis of a methanol extract of *A. fruticulosus* leaves indicated the presence of four highly sweet cycloartane glycosides that were isolated from the leaves of *Abrus precatorius*. These compounds, abrusosides A-D, have been structurally characterized as a result of spectroscopic and X-ray crystallographic determinations. In this example, a rapid isolation method was developed for abrusosides A-D using a combination of high-speed centrifugal counter-current chromatography (HSCCC), flash column chromatography and over-pressured layer chromatography (OPLC). In this manner, it has been possible to compare the yields of abrusosides A-D in *A. fruticulosus* and *A. precatorius.*

*Abrus fruticulosus* was cultivated at Maehongson Province Forestry Station in Thailand.

The dried leaves (250 g) of *A. fruticulosus* are exhaustively macerated with 80% MeOH to afford 98.4 g of a residue on removal of solvent. A portion of this residue (70 g) is taken up in $H_2O$ (500 ml), defatted with diethyl ether (5×500 ml), adusted to pH 3, and extracted with 1-butanol (3×1 liter). Upon drying, a BuOH-soluble residue (18 g) is obtained, which is then triturated with volumes of MeOH (250 ml total), to afford a light-brown precipitate (2.4 g), that appears to contain all of abrusosides A-D originally present in the plant when examined by TLC. A 2.0-g portion of this MeOH-insoluble precipitate is subjected to HSCCC (Multilayer Coil Plant Instrument equipped with a 2.6 mm i.d. coil, P.C., Inc., Potomac, Md., USA) on a batchwise basis (4×0.5 g), using $CHCl_3$-MeOH-$H_2O$ (7:13:8) as solvent, with the lower layer as mobile phase, at a flow rate of 1.5 ml/min. A coil speed of 800 rpm was used, and the solute was applied after dissolution in 1:1 v/v mixture (5-6 ml) of the mobile and stationary phases. Fractions (10 ml each) are pooled subsequent to TLC examination, and quantities of impure abrusoside A (70 mg), abrusoside C (224 mg), and abrusosides B and D (500 mg) are found to be present in HSCCC fractions 6-8, 9-11, and 30-36, respectively. This HSCCC procedure provides a rapid preliminary separation of abrusosides A-D.

Final purification of abrusoside A in HSCCC fractions 6-8 is conducted by flash column chromatography, by isocratic elution with $CHCl_3$-MeOH-$H_2O$ (6:3:1, lower layer) over a column (45 cm × 2.5 cm, i.d.) containing 20 g of silica gel, at a flow rate of 5 ml/min. When 8-ml fractions are collected, pure abrususide A 4.2 mg, 0.003% w/w) is eluted in fractions 4-5. Separate application of these same flash column chromatographic conditions to a portion of HSCCC fractions 30-36 (100 mg) afforded pure abrusoside B (25 mg, 0.084% w/w) and abrusoside D (51.7 mg, 0.174% w/w) in fractions 7-8 and 29-39, respectively.

Since it was not practical after preliminary HSCCC to resolve abrusoside C from pigment impurities with flash column chromatography, this compound is purified by OPLC (Chrompres 25 instrument, Labor Mim, Budapest, Hungary), using the same solvent system and chromatographic conditions previously employed for the preparative separation of the sweet steroidal saponin, polypodoside A. Separation in this manner of a 50-mg portion of HSCC fractions 9-11 affords pure abrusoside C (24.1 mg 0.073% w/w).

The identity of the purified abrusosides A-D from *A. fruticulosus* was determined by negative-ion fast-atom bombardment (FAB) mass spectrometry: (glycerol), A, [M-H]+ m/z 645; B, [M-H]+ m/z 835; C, [M-H]+ m/z 807; D, [M-H]+ m/z 821. The compounds are also compared with authentic samples of abrusosides A-D (1-4) by mp, optical rotation, $^{13}C$-NMR, and TLC in several systems.

What is claimed is:

1. A substantially pure compound having the formula:

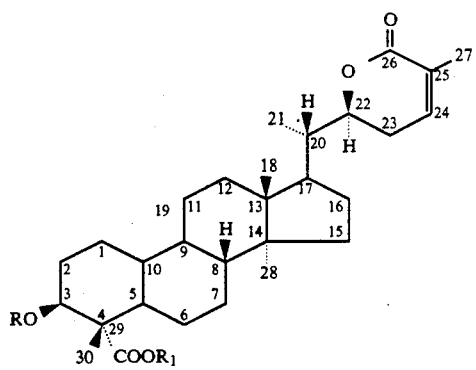

and food-acceptable salts thereof wherein R is beta-glucuronopyranosyl-6-methyl ester[2]betaglucopyranosyl, betaglucopyranosyl[2]-beta-glucopyranosyl, or beta-glucuronopyranosyl[2]-beta-glucopyranosyl; and $R_1$ is H or lower alkyl.

2. The compound according to claim 1 wherein $R_1$ is H.

3. A substantially pure compound having the formula:

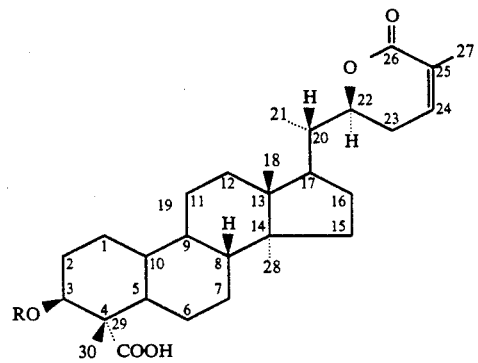

and food-acceptable salts thereof, wherein R is beta-glucuronopyranosyl -6-methyl ester[2]betaglucopyranosyl.

4. A substantially pure compound having the formula:

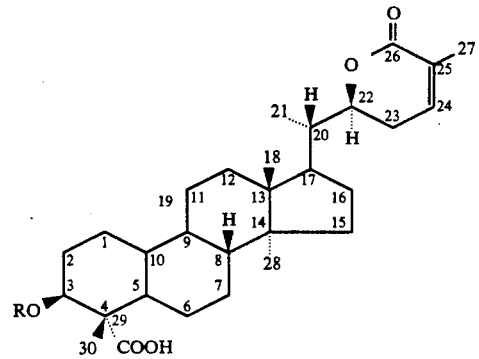

and food-acceptable salts thereof, wherein R is beta-glucopyranosyl[2]-beta-glucopyranosyl.

5. A substantially pure compound having the formula:

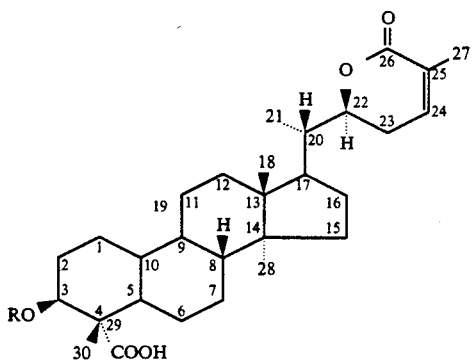

and food-acceptable salts thereof, wherein R is beta-glucuronopyranosyl$^2$-beta-glucopyranosyl.

6. A composition containing as the active ingredient a compound according to any one of claims 1 or 3–5 in a carrier system.

7. A sweetening composition comprising a sweetening effective amount of a compound according to any one of claims 1 or 3–5 and a food-acceptable carrier therefor.

8. The composition according to claim 7 wherein said compound is present in an amount ranging from about 0.001 to about 0.5 wt %.

9. A method of sweetening and enhancing the flavor of foodstuffs or medicinal agents, comprising adding to said foodstuffs or medicinal agents a sweetening effective amount of a compound according to any one of claims 1 or 3–5.

10. The method of claim 9 wherein the foodstuff is selected from the group consisting of flavored chewing gum products.

11. The method of claim 9 wherein the foodstuff is selected from the group consisting of flavored breathmint products.

12. The method of claim 9 wherein the foodstuff is an imitation meat product.

13. The method of claim 9 wherein the foodstuff is selected from the group consisting of vegetable proteins, soy sauce, and beam paste.

14. The method of claim 9 wherein the medicinal agent is selected from the group consisting of chewable vitamins and aspirin.

15. The method of claim 9 wherein the foodstuff or medicinal agent is a solid composition.

16. The method of claim 9 wherein the foodstuff is selected from the group consisting of chocolate.

17. The method of claim 9 wherein the foodstuff is selected from the group consisting of orange, cherry and strawberry flavored juice or beverage products.

18. The method of claim 9 wherein the medicinal agent is selected from the group consisting of mouthwashes and aerosol breath deodorants.

19. The method of claim 9 wherein the foodstuff or medicinal agent is a liquid composition.

20. The method of claim 9 wherein the effective amount of the compound is within the range of from about 0.001 to about 0.5 wt %.

21. The method of claim 9 wherein the effective amount of the compound is within the range of from about 0.01 to about 0.50 grams per liter of aqueous solution.

22. The method according to claim 9 wherein said medicinal agents are orally administered.

* * * * *

UNITED STATES PATENT AND TRADEMARK OFFICE
CERTIFICATE OF CORRECTION

PATENT NO. : 5,198,427
DATED : March 30, 1993
INVENTOR(S) : Douglas A. Kinghorn, et al.

It is certified that error appears in the above-identified patent and that said Letters Patent is hereby corrected as shown below:

Column 5, lines 8-22: " 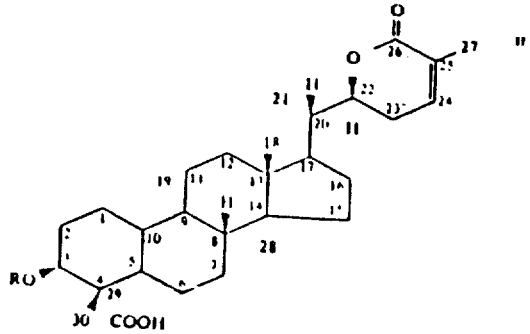 "

should read as -- 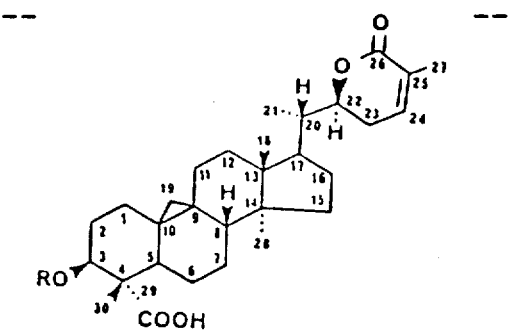 --

Column 5, line 28: "beta-glucuronopyranosyl$^{12}$" should read as --beta-glucuronopyranosyl$^2$--

Column 8, line 30: "Et20" should read --Et$_2$O--

UNITED STATES PATENT AND TRADEMARK OFFICE
CERTIFICATE OF CORRECTION

PATENT NO. : 5,198,427

DATED : March 30, 1993

INVENTOR(S) : Douglas A. Kinghorn, et al.

Page 2 of 3

It is certified that error appears in the above-identified patent and that said Letters Patent is hereby corrected as shown below:

Column 9, line 48: "C-1)" should read --C-1')--

Column 9, line 64: "699" should read --669--

Column 9, line 65: "699" should read --669--

Column 10, line 37: "($C_8H_{11}O_3$" should read --($C_8H_{11}O_2$--

Column 10, line 44: "tic" should read --tlc--

Column 10, line 44: "solvents 3" should read --solvents 2--

Column 10, line 51: "44" should read --4.4--

Column 10, line 61: after "19" delete --)--

Column 10, line 66: "(3)" should read --(4)--

Column 11, line 18: "170.79" should read --17-.79--

Column 11, line 40: "1 H" should read --3 H--

Column 11, line 50: "OCH$)_3$)" should read --OCH$_3$)--

Column 11, line 61: "Nz" should read --Na--

UNITED STATES PATENT AND TRADEMARK OFFICE
CERTIFICATE OF CORRECTION

PATENT NO. : 5,198,427
DATED : March 30, 1993
INVENTOR(S) : Douglas A. Kinghorn, et al.

It is certified that error appears in the above-identified patent and that said Letters Patent is hereby corrected as shown below:

Column 11, line 63: "649" should read --849--
Column 12, line 11: "$cm^1$" should read --$cm^{-1}$--
Column 12, line 20: "C-2" " should read --C-2'--
Column 12, line 25: "29,63" should read --29.63--
Column 12, line 41: "tic" should read --tlc--
Column 14, line 29: "254" should read --1254--

Signed and Sealed this

Fifteenth Day of March, 1994

BRUCE LEHMAN

*Attest:*

*Attesting Officer*  *Commissioner of Patents and Trademarks*

UNITED STATES PATENT AND TRADEMARK OFFICE
CERTIFICATE OF CORRECTION

PATENT NO. : 5,198,427
DATED : March 30, 1993
INVENTOR(S) : Douglas A. Kinghorn, et al.

It is certified that error appears in the above-indentified patent and that said Letters Patent is hereby corrected as shown below:

In the Drawings, FIG. 2:

" FIG.2 STRUCTURE OF ABRUSOSIDES A-D AND ABRUSOGENIN. "

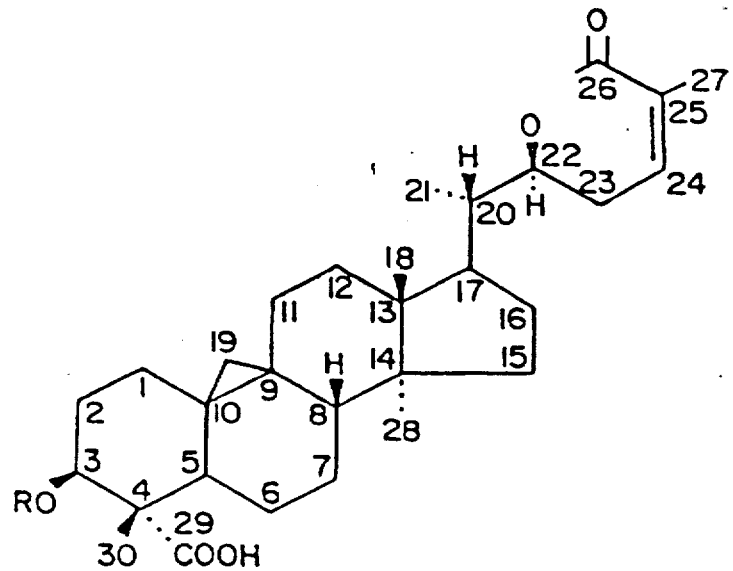

ABRUSOGENIN (R=H)
ABRUSOSIDE A (R=$\beta$-glc)
ABRUSOSIDE B (R=$\beta$-glcA-6-methyl ester$^2$-$\beta$-glc)
ABRUSOSIDE C (R=$\beta$-glc$^2$-$\beta$-glc)
ABRUSOSIDE D (R=$\beta$-glcA$^2$-$\beta$-glc)

UNITED STATES PATENT AND TRADEMARK OFFICE
CERTIFICATE OF CORRECTION

PATENT NO. : 5,198,427
DATED : March 30, 1993
INVENTOR(S) : Douglas A. Kinghorn, et al.

It is certified that error appears in the above-indentified patent and that said Letters Patent is hereby corrected as shown below:

should read as

-- FIG.2 STRUCTURE OF ABRUSOSIDES A-D AND ABRUSOGENIN. --

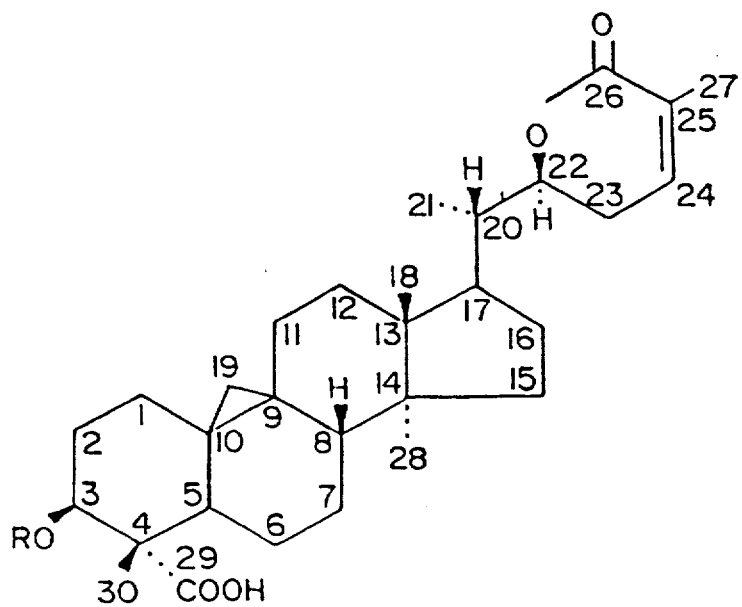

ABRUSOGENIN (R=H)
ABRUSOSIDE A (R=$\beta$-glc)
ABRUSOSIDE B (R=$\beta$-glcA-6-methyl ester$^2$-$\beta$-glc)
ABRUSOSIDE C (R=$\beta$-glc$^2$-$\beta$-glc)
ABRUSOSIDE D (R=$\beta$-glcA$^2$-$\beta$-glc)

UNITED STATES PATENT AND TRADEMARK OFFICE
CERTIFICATE OF CORRECTION

PATENT NO. : 5,198,427
DATED : March 30, 1993
INVENTOR(S) : Douglas A. Kinghorn, et al.

It is certified that error appears in the above-indentified patent and that said Letters Patent is hereby corrected as shown below:

Column 4, lines 26-39:

" 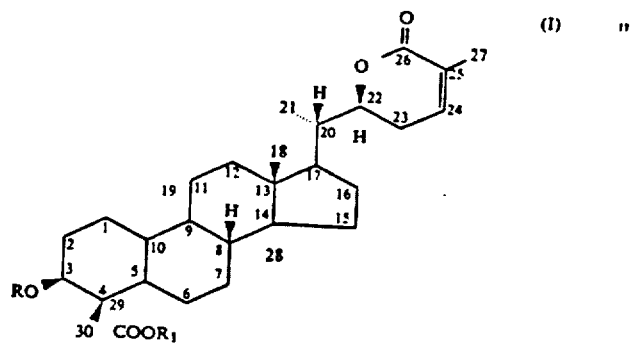 (I) "

should read as

-- 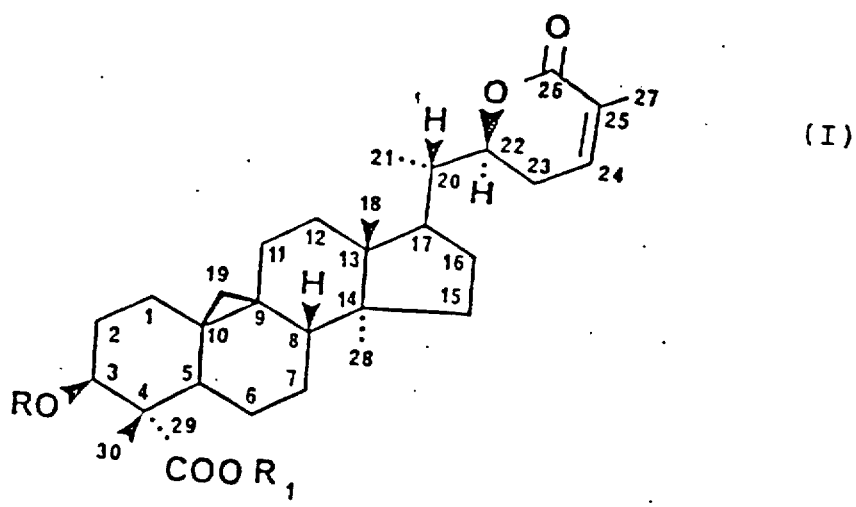 (I) --

UNITED STATES PATENT AND TRADEMARK OFFICE
CERTIFICATE OF CORRECTION

PATENT NO. :   5,198,427
DATED      :   March 30, 1993
INVENTOR(S):   Douglas A. Kinghorn, et al.

It is certified that error appears in the above-indentified patent and that said Letters Patent is hereby corrected as shown below:

Column 16, line 47:   "expect"   should read
--except--

Column 18, lines 1-8, Claim 1:

"
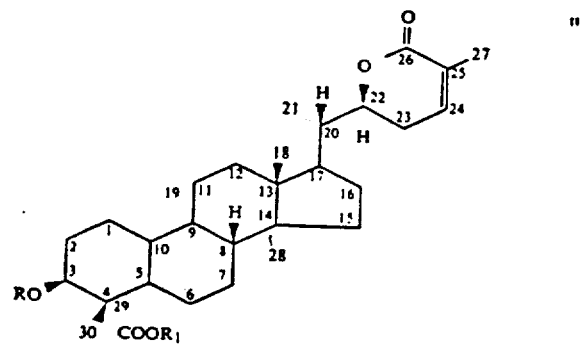
"

should read as

UNITED STATES PATENT AND TRADEMARK OFFICE
CERTIFICATE OF CORRECTION

PATENT NO. : 5,198,427
DATED : March 30, 1993
INVENTOR(S) : Douglas A. Kinghorn, et al.

It is certified that error appears in the above-indentified patent and that said Letters Patent is hereby corrected as shown below:

--

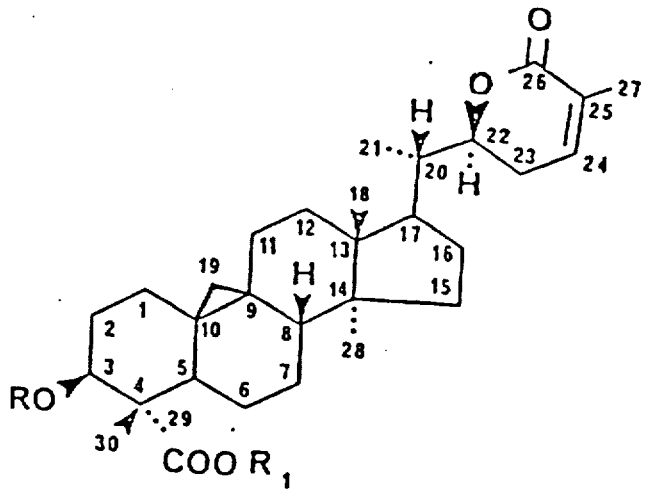

Column 18, lines 30-44, Claim 3:

"

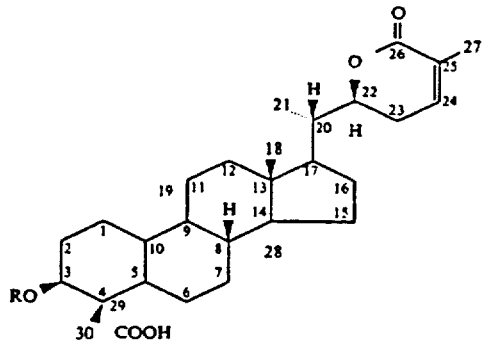

"

should read as

--

UNITED STATES PATENT AND TRADEMARK OFFICE
CERTIFICATE OF CORRECTION

PATENT NO. : 5,198,427
DATED : March 30, 1993
INVENTOR(S) : Douglas A. Kinghorn, et al.

Page 6 of 9

It is certified that error appears in the above-indentified patent and that said Letters Patent is hereby corrected as shown below:

--

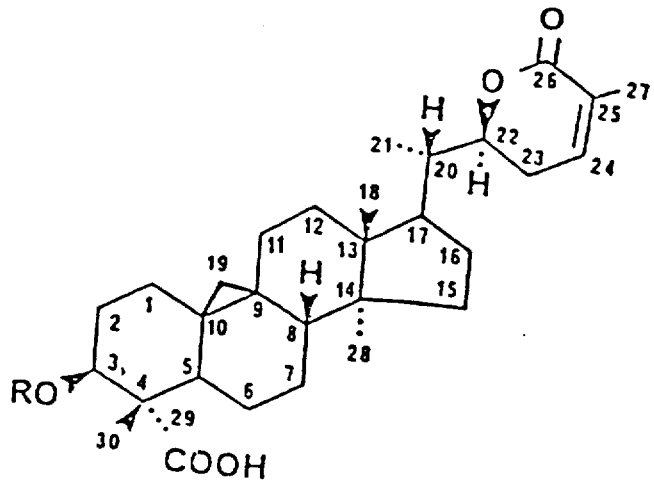

Column 18, lines 51-65, Claim 4:

"

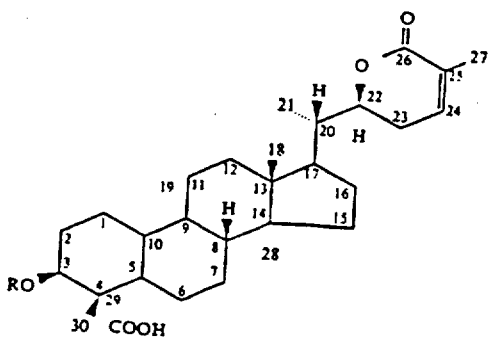

"

--

UNITED STATES PATENT AND TRADEMARK OFFICE
CERTIFICATE OF CORRECTION

PATENT NO. : 5,198,427
DATED : March 30, 1993
INVENTOR(S) : Douglas A. Kinghorn, et al.

It is certified that error appears in the above-indentified patent and that said Letters Patent is hereby corrected as shown below:

should read as

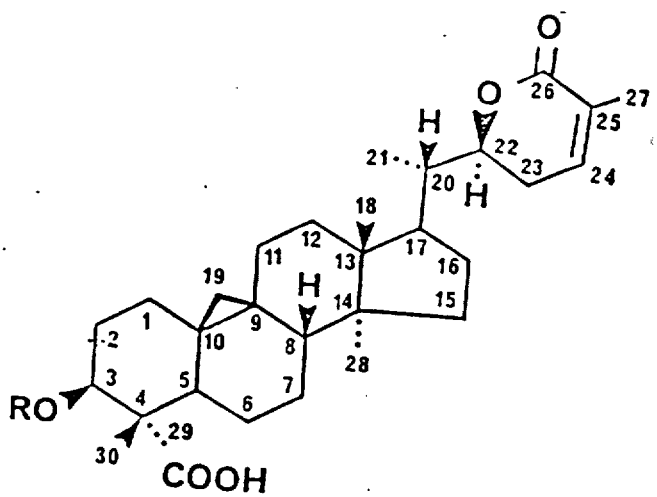

UNITED STATES PATENT AND TRADEMARK OFFICE
CERTIFICATE OF CORRECTION

PATENT NO. : 5,198,427
DATED : March 30, 1993
INVENTOR(S) : Douglas A. Kinghorn, et al.

It is certified that error appears in the above-indentified patent and that said Letters Patent is hereby corrected as shown below:

Column 19, lines 3-18, Claim 5:

"

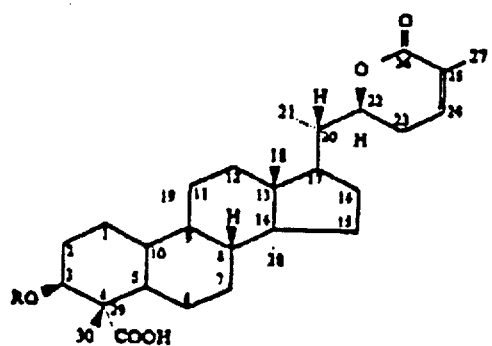

"

should read as

--

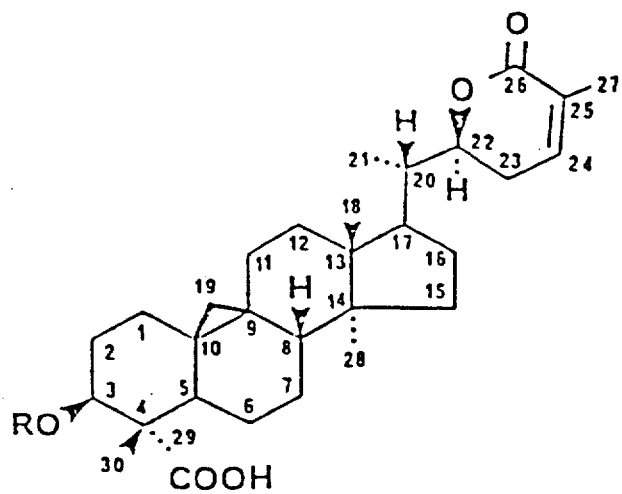

--

UNITED STATES PATENT AND TRADEMARK OFFICE
CERTIFICATE OF CORRECTION

PATENT NO. : 5,198,427
DATED : March 30, 1993
INVENTOR(S) : Douglas A. Kinghorn, et. al.

It is certified that error appears in the above-indentified patent and that said Letters Patent is hereby corrected as shown below:

Column 11, line 18, "17-.79" should read --170.79--.

Signed and Sealed this

Thirteenth Day of December, 1994

Attest:

BRUCE LEHMAN

*Attesting Officer*     *Commissioner of Patents and Trademarks*